(12) United States Patent
Dodds

(10) Patent No.: US 6,287,254 B1
(45) Date of Patent: Sep. 11, 2001

(54) ANIMAL HEALTH DIAGNOSIS

(76) Inventor: W. Jean Dodds, 938 Stanford St., Santa Monica, CA (US) 90403

( * ) Notice: Subject to any disclaimer, the term of this patent is extended or adjusted under 35 U.S.C. 154(b) by 0 days.

(21) Appl. No.: 09/432,851

(22) Filed: Nov. 2, 1999

(51) Int. Cl.$^7$ ....................................................... A61B 5/00
(52) U.S. Cl. .......................... 600/300; 128/920; 128/904
(58) Field of Search .................................... 600/300–301; 128/897–898, 903, 904, 920–925; 705/2–3; 434/236

(56) References Cited

U.S. PATENT DOCUMENTS

| | | |
|---|---|---|
| 5,817,025 | 10/1998 | Alekseev et al. . |
| 5,830,709 | 11/1998 | Denson et al. . |
| 5,911,687 | 6/1999 | Sato et al. . |
| 5,954,640 * | 9/1999 | Szabo ..................................... 600/300 |
| 6,063,028 * | 5/2000 | Luciano ................................ 600/300 |
| 6,081,786 | 6/2000 | Barry et al. . |
| 6,135,055 | 10/2000 | Pratt . |
| 6,232,522 | 5/2001 | Harley et al. . |

* cited by examiner

Primary Examiner—Robert L. Nasser
Assistant Examiner—Michael C Astorino
(74) Attorney, Agent, or Firm—Oppenheimer, Wolff & Donnelly LLP

(57) ABSTRACT

Laboratory test data are analyzed in relation to the health assessment data of an animal together with the genetic data related to that same animal. These data are relevant to the likely morbidity, likely longevity, and/or the potential risk for disease or disorder for the animal, including temperament, immune stimulation and cellular inflammatory response mediators, markers for neoplastic or paraneoplastic change, inherited organ dysfunction or dysplasia, autoimmune thyroiditis, mammary cancer, immune surveillance markers, and inherited bleeding tendency. A panel of tests relates to at least one of endocrine function, immunologic function, gastrointestinal function and nutritional analysis, inborn errors of metabolism, paternity, DNA fingerprinting, hemostasis and coagulation function, vaccinal antibody status, adverse and potential adverse vaccine reaction, infectious diseases, pathology, blood typing and bone marrow analysis, cell cytotoxicity, cytokine and allergy testing, and markers of neoplastic and paraneoplastic change.

14 Claims, 7 Drawing Sheets

ANIMAL HEALTH DIAGNOSIS

RELATED APPLICATION

This application relates to application Ser. No. 09/419,192 (Dodds) entitled Animal Genetic And Health Profile Database Management, and filed Oct. 15, 1999, the contents thereof are incorporated by reference herein.

TECHNICAL FIELD

This invention is concerned with animal health diagnosis. More particularly the invention is directed to the testing, diagnosis and prediction of diseases and disorders of animal companions, for instance dogs and cats.

Further this invention relates to a method, system and apparatus for the management of comprehensive and cumulative genetic and health assessment databases in relation to animals worldwide. In particular, the invention relates to a bioinformatics system and its implementation in relation to animal biological data.

BACKGROUND OF THE INVENTION

Breeders, owners, and caregivers of animals which can be companions, such as dogs, cats, horses, farm, food, or zoo animals, and wildlife, have a need to understand their physical and biological attributes, genetic makeup, heritable disease, and disorder background, and longevity.

Substantial investments in time, effort and financial resources are made by the breeders, owners, and caregivers of these animals, particularly purebred animals, to characterize their health state and predict their morbidity, mortality and longevity. Resources are separately directed to obtaining information about their genetic background. There is also a need to conduct periodic comprehensive health assessments of animals.

The probability that an individual animal will develop a specific health-related condition in its lifetime is a product of complex interactions between its genetic makeup, environmental influences including diet, and agents of disease (e.g., chemical, physical, or biological) that it encounters. Perhaps the best indicator of overall health of an individual animal or breed is longevity.

The physical attributes, and other descriptve and health assessment information is generally termed in this application as the phenotypic information. Genetic disorder information is termed in this application as the genotypic information. Generally, these are two distinct and differing sets of information.

Phenotype Data

The physical descriptive and health assessment profiles include characteristics such as the physiological, pathological, endocrinological, hematological, epidemiological, behavioral, and immunological data from parameters such as phenotype, breed, lifespan, health history, and presence of infectious diseases and metabolic disorders. All of this is part of the phenotypic information. A health assessment profile of an animal typically relates to a particular subject of the group, as opposed to the group of animals as a whole. Generally, the phenotype is the genetic nature of an organism that is revealed by visible characteristics or measurable performance, in contradistinction to the genotype, which may not be evident without a breeding test or genetic map.

Laboratories having a central database processing resource (CDPR) as well as in-office laboratory equipment at veterinary hospitals or clinics are used for analyzing blood and other biological samples of a subject animal. This is a system for obtaining the phenotypic information. Communication systems are known for connecting these laboratories with veterinary clinics through a telephone and/or fax connection on an automated basis. These systems permit the veterinarian, animal hospital, or other authorized person (collectively or individually termed the "remote user") to receive the health assessment profile and basic descriptive identifying data, namely phenotypic information, of a subject animal from the CDPR. Until recently, it was not possible for the remote user to access the CDPR directly to obtain this phenotypic information of a subject animal.

It is known for the breeder and/or owner of animals, such as purebred companions in the nature of dogs, cats, and horse, or animals of mixed breeding, to obtain health assessments of their animals. The owners obtain these data by submitting blood or other body fluid and tissue samples of their animals, usually through a veterinarian or veterinary clinic, to a laboratory for analysis of the biological, physiological, or pathological condition, namely the physical health of the animal. These data are then reported to the owner through the veterinarian or veterinary clinic. The data also can be stored on the CDPR of the laboratory. Additionally, for each subject animal, the phenotypic data can be stored on a computer storage system at the veterinary clinic or in a computer storage system of the owner and/or breeder. The retrieval of the data can be electronically, by voice, hard copy, or fax as required.

Seeking, obtaining and storing this phenotypic information is driven by the needs of the animal breeder, owner or the agent of the owner and the animal's healthcare provider. This information is of a nature that it is the primary information sought to resolve the clinical, diagnostic, management, and therapeutic needs of an animal subject when the animal is in need of periodic wellness examination, is ill, or is to be restored to a well condition. These data are the essential information resorted to by the clinician in the care of animals.

Genotype Data

The genotypic information relates to genetic mapping, genetic background, and genetic screening databases. This includes data obtained from the pedigree, family history, heritable physical characteristics, genetic screening tests, DNA testing, genomic mapping, and related laboratory assessment of the gene product for known or suspected congenital and heritable traits. In this application, the term "gene product" means the specific phenotypic characteristic (s) resulting from the expression of the genotype, and may include certain specific laboratory test data.

This second aspect of data associated with the animals is the genetic or genotype data or information. These data are typically used to estimate the presence and prevalence of disease or disorder among different breeds or kinds of animals. These data are currently available on some select clinical research databases, in book form, hard copy, or in genetic disease registries.

When retained in a genetic disease registry, the data typically list only those animals that are not affected with or carrying the heritable trait in question. The abnormal or non-normal conditions (affected with or carriers of the heritable trait) are normally the subject of confidential knowledge of a breeder and/or owner, and not the subject of a generally accessible database. This is retained as confidential by the owners either for financial reasons, risk reasons, legal liability reasons, or personal reasons.

The genotypic information typically relates to-individual animals, or a group or class of animals and is most often stored manually in a non-CDPR facility. It is not typically stored by veterinarians in a clinical setting, since the genotypic data is a specialist form of data used mainly for cataloging and research of diseases and disorders among animals. It is also not generally available for access to assist in the clinical analysis, diagnosis, and therapeutic management of animals.

This genotypic information, namely the physical characteristics and genetic makeup pedigree), heritable disorder history, and related health history of animals in the group is usually manually recorded by breeders, owners, and researchers of companion and other valued animals. The genetic constitution of an organism includes genes without visible effects as well as those revealed by the phenotype. It may refer to all the genes or to a single pair of alleles. The genotypic information is transmitted manually to and from persons or local and national genotypic databases maintained for specific disorders, and designed to foster research into diseases and disorders, rather than being readily accessible to users for clinical purposes in the manner of phenotypic data on a CDPR.

Some of the genetic data are available on registries related to specific diseases or disorders, for instance, hip dysplasia, eye conditions, thyroid conditions, and blood conditions. Such disease-specific registries are usually set up either by identifying affected animal breeds, or are indexed by disease or disorder. The genetic information databases are generally closed (kept confidential), but in some cases may be open to researchers or members of groups, associations, and clubs.

Failings of the Existing Systems

To promote better health among animals, which can be animal companions, sport animals, farm animals, and the like, such as canine, feline, equine, bovine, porcine, caprine, ovine, and zoo animals or wildlife, it is important to secure accessible genotypic or genetic information databases. It is also important to be able to relate these genotypic databases to the health assessment profiles or phenotypic databases of particular subject animals.

Many purebred animals are valuable, and so it is important to obtain their descriptive phenotypic information, and periodic health assessment data throughout their lives, and also to incorporate their genotypic information in order to promote and maintain effective high quality and healthy breeding stock, and maximize their lifespan. The phenotype data for an animal include the health assessment profile, breed, and the physical characteristics of the animal. The genotype data include the genetic map, pedigree, family history, genetic screening tests, and disorder and disease characteristics of a particular animal, animal family, line, or group of animals.

There is a need to develop these data in a cumulative, comprehensive, and dynamic system of database management to thereby enhance the health predictability, and longevity of animals.

This type of comprehensive and cumulative database on individual or groups of animals needs to be preserved and shared locally, regionally, nationally, and globally. A mechanism to do this is presently not known due to the various constraints surrounding each of the two types of databases. The phenotype database storage, use, and access is fashioned, formed and structured for use by clinical laboratories and veterinarians. The genotype information is fashioned and structured generally for clinical research and breeder/owner uses as opposed to clinical medical uses.

It is not known to store and/or present phenotypic information and genotypic information as a comprehensive and cumulative assessment of individual animal subjects, families of subjects, breeds of subjects, or species of animals in a computerized format which is available through computer networlding to authorized remote users.

Accordingly, there is a need to relate different databases from animals, animal groups or species, in a manner to permit enhancement of the animal kingdom for breeding and growth in a healthy manner with a minimum of disease (reduced morbidity and mortality) and increased longevity.

As the above demonstrates, there is a need for a new database management bioinformatics scheme and relational database, together with computerized networks that manage, analyze, and/or integrate comprehensive and cumulative animal health assessment data and genetic identifier, genomic mapping, and genetic assessment data A comprehensive approach to animal health and genetic selection or management of animals, and their clinical care is the subject of the present invention.

Current laboratory and research systems and computerization have not achieved this, and nor have communication protocols been used effectively in this technological area to facilitate such a relationship or relational bioinformatics database system for management and dissemination of this comprehensive and cumulative information.

More specifically, it is necessary in animal health diagnosis and care that appropriate predictive testing for diseases and disorders of animals be achieved in order to reduce morbidity and mortality, and improve the quality of life and lifespan. Currently this is not done in relation to the health assessment data of an animal together with the genetic data related to that same animal. Current tests do not provide as much data as possible to attain correct diagnosis and disorder predictions with the net result of an improvement in the quality of life and increased longevity. Moreso, currently available testing is unnecessarily complex and expensive in relation to the ability to be an accurate predictor of diseases and disorders in animals, and hence their likely longevity.

SUMMARY OF THE INVENTION

The invention is directed to a method, apparatus and system of obtaining, analyzing and reporting laboratory test data in relation to the health assessmant data of an animal together with the genetic data related to that same animal.

These data include a panel of tests related to at least one of endocrine function, immunologic function, gastrointestinal function and nutritional analysis, inborn errors of metabolism, paternity, DNA fingerprinting, hemostasis and coagulation function, vaccinal antibody status, adverse and potential adverse vaccine reaction, infectious diseases, pathology, blood typing and bone marrow analysis, cell cytotoxicity, cytokine and allergy testing, and markers of neoplastic and paraneoplastic change. These data are relevant to the likely morbidity, likely longevity, and/or the potential risk for disease or disorder for the animal.

According to one aspect of the invention, health profiling of an animal is effected to determine characteristics related to the temperament of the animal which impacts on its longevity. Biological laboratory test data from a bodily fluid or tissue of an animal are analyzed. Such test data relate to the level of neurotransmitter activity of the animal. The data relate to at least one of the value of serotonin, the gamma-aminobutyric acid (GABA), the dopamine, the norepinephrine, the histamine, or the other neuropeptides of the animal. The value should fall within predetermined levels as a predictive determinant of the animal's temperament (passivity, assertiveness, or aggressivity).

One other aspect of the invention relates health profiling of an animal to determine characteristics related to at least one of the immune stimulation reaction, evidence of neoplastic or paraneoplastic change, or the cellular inflammatory response of the animal. Biological laboratory test data from a bodily fluid or tissue of an animal are analyzed. The test data relates to at least one of cell cytotoxicity markers, cytokine and chemokine levels, immunoglobulin levels, type and amount of lymphocyte subsets and lymphocyte markers, and markers of neoplastic or paraneoplastic change of the animal. The value should fall within predetermined levels as a determinant of the immune stimulation reaction, neoplastic or paraneoplastic change, or the cellular inflammatory response.

According to another aspect of the invention, health profiling of an animal determines characteristics related to inherited organ dysfunction or dysplasia of the animal, at least one of which is neuronal, neuromuscular or renal. Biological laboratory test data from a bodily fluid or tissue of an animal are analyzed. The test data relate to an amino acid, carbohydrate, lipid or other metabolic component, body fluid or tissue marker of the animal. The data includes obtaining data related to at least one of the value of the methyl malonic acid, the fucose-containing cell metabolites, uric acid, normoglycemic glycosuria, amino acid uria, mannosidase containing cell metabolites, amyloid deposition in tissues, neuronal ceroid lipofuscin deposition, and deposition of gangliosides and other lysomal storage substrates of the animal. The value should fall within predetermined levels as a determinant of the inherited organ dysfunction or dysplasia.

According to a further aspect of the invention, health profiling of an animal determines characteristics related to autoimmune thyroiditis of the animal. Biological laboratory test data from a bodily fluid or tissue of an animal are analyzed. The test data relate to a physiologic or genetic marker for autoimmune thyroiditis of the animal. The data relates to at least one of the results of a comprehensive thyroid autoantibody test profile, DNA fingerprint (the gene map), and markers for immunoglobulin receptors on B-cells, T-cell receptors, and protein products of the major histocompatibility complex (AMC) genes (Class I and II allellic HLA, DLA or equivalent antigenic specificities) of the animal. Example assays to screen for MHC genes include restriction fragment length polymorphism (RFLP), polymerase chain reaction (PCR) RFLP, PCR sequence-specific oligonucleotides (SSO) and PCR sequence-specific primers (SSP). The values should fall within predetermined levels as a determinant of autoimmune thyroiditis.

According to a further aspect of the invention, health profiling of an animal determines characteristics related to presence of or susceptibilty to mammary cancer of the animal. Biological laboratory test data from a bodily fluid or tissue of an animal are analyzed. The test data relate to estrogen (estradiol-17β), estrogen receptors, interleukin (IL) 6, progesterone, and progesterone receptors. The value should fall within predetermined levels as a determinant of presence or susceptibility to mammary cancer.

According to a further aspect of the invention, health profiling of an animal determines characteristics related to the tissue environment of the eye and brain (ocular and blood-brain barrier) which are sites protected from the normal immunologic surveillance mechanisms. Biological laboratory test data from a bodily fluid or tissue of an animal are analyzed. The test data relate to the soluble and cellular immune inflammatory response mediators (cytokine and chemokine levels, immunoglobulin levels, and lymphycyte susbset markers). The value should fall within predetermined levels as a determinant of integrity of protected immune surveillance mechanisms.

According to a further aspect of the invention, health profiling of an animal determines characteristics related to the tendency to bleed excessively are determined. Biological laboratory test data from a bodily fluid or tissue of an animal are analyzed. The test data relate to a comprehensive assessment of the hemostatic and coagulation function. The value should fall within predetermined levels as a determinant of the presence of bleeding disorder.

The invention includes obtaining genetic data related to the animal, and relating the generic data related to that animal with the biological data. Also the profiling includes obtaining data related to the current health condition of the animal.

More particularly the invention comprises combining genetic data of animals with health assessment data of animals thereby to permit an analysis predicting health, disease and disorder probabilities and longevity of selected animals the combination is analyzed, and a report is provided to a remote user based on the analysis the health assessment data of the animal and the genetic data In light of the above, there is provided by this invention a system for managing animal diagnosis, including the performance of specific tests. The phenotypic and genotypic data and information relating to animals, particularly purebred animals can be used to enhance the prediction of disease and/or disorder.

The invention also provides a bioinformatics system for inputting, controlling, analyzing and outputting of a broad range of criteria related to the health, genetic background and longevity of animals. This includes a system concerning phenotype data and genetic data relating to animals. Further, there is provided a system for screening of genetic data and genomic mapping, and integrating the phenotype health assessment data and genetic identifier and assessment data in a CDPR. Moreover, there is provided a system for analyzing the health assessment or phenotypic data with the interrelated genetic or genotypic data. Thereafter, those data and analyses are communicated from the CDPR in a broad range and in a manner that has not previously been possible.

The present invention offers a unique solution to above-described problems by providing an apparatus, method and system, in relation to animals, for performing data analyses of biological specimens from specific subject animals or animal groups in relation to specific subject animal or animal groups of genetic data. The apparatus, method and system comprises a controller for obtaining, inputting, and analyzing biological, physiological, and pathological test data together with genomic mapping and genetic screening data into the CDPR.

The biological, physiological, and pathological data of the subject animal or animal group and the genetic data of the subject animal or animal group are communicated to a remote user as raw data or as related, analyzed biological, physiological, and pathological data and genetic data. The remote user can also appropriately access the CDPR to input data to, or obtain data from, the CDPR.

The CDPR includes at least two databases, one of the databases contains genetic information in relation to animals and the other is a phenotypic database.

The genetic database is either a specific file of a selected animal or a generalized animal database relating to group characteristics, and is cross-relatable with the phenotypic database of particular selected subject animals.

Additionally other databases can be used and cross-related to these databases. The genetic database includes data from selected animals, animal families, animal breeds and/or data related to selected animal diseases and/or disorders. Other databases include those related to genetic markers or maps of animals, databases related to epidemiology, purebred animal ownership, identification registries, and studbook registries.

The phenotype, health profile, or health assessment database contains data which is mostly phenotypic. The genotype database includes data which is in the category of mostly genotype or genetic and which may include a second category of some phenotype data which predicts or manifests the genotype and genetic data. The invention includes relating the phenotypic data to either one or both types of the genotypic data.

Information in the databases are used to build computer driven statistical models to predict the occurrence of specific diseases and longevity for individual animals on a breed-by-breed or family and group basis. Multivariate statistical techniques are used including multiple regression, logistic regression, and Cox proportional hazards. As new diagnostic technology and genomic information become available, the database is continually expanded and the statistical models are updated to enhance predictive ability. This ability to predict the occurrence of disease or disorder is used to develop and evaluate screening programs in veterinary medicine in order to detect disease earlier, thereby improving the outcome and quality of life for animals and their owners. The information is also used to design disease prevention programs based on dietary/environmental modification and selective breeding. The database is also used to explore previously unsuspected relationships between specific diseases such as cancer and diet, vaccination, or chemical exposures. There There is provided means for inputting data into the genetic database and phenotypic database, and other databases, storing the data in these databases, analyzing the data in a relational sense from the different databases, and retrieving the data from these databases, namely the databases which are part of the CDPR.

A further aspect of the invention is the accessibility of the health assessment database and/or genetic database or other databases of the CDPR by the remote user selected on the basis of password, security control, and financial payment such that the data can be transmitted into and from the CDPR by a computer network. Use of selected passwords, encryption systems, and payment systems are employed to facilitate and restrict the flow of data in and/or out of the databases. Alerts can be set up to advise of attempts at unauthorized access to the CDPR. The computer network may conveniently include the Internet.

As required, the data in the CDPR can also be distributed to multiple authorized remote parties, namely third parties for research or other analysis. The invention also includes a method and system for achieving this.

Further aspects of the present invention will become apparent in the course of the following description and by reference to the attached drawings.

DETAILED DESCRIPTION OF THE PREFERRED EMBODIMENT

Figure 1:
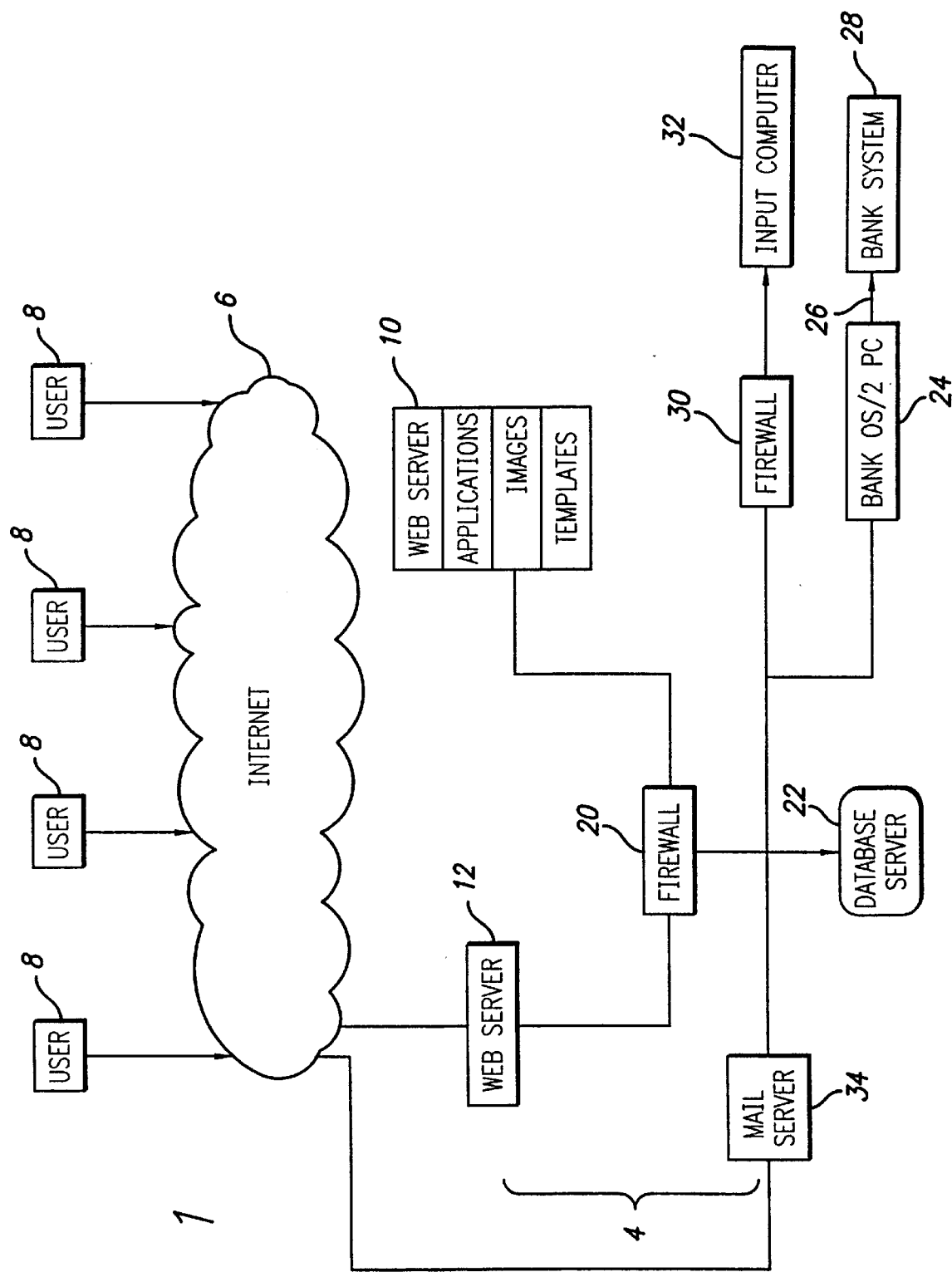
FIG. 1 is an overall view of a web-based system to provide access to a database management system of an animal genetic database and a health assessment database of the invention, in relation to the Internet.

The present invention will now be described in detail with reference to a few preferred embodiments thereof, as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order to not unnecessarily obscure the present invention.

Genetic Screening and Counseling of Purebred Animals

The common practice to line-breed and inbreed purebred animals facilitates the transmission and recognition of congenital and heritable defects. Large-scale screening programs for the identification of genetically affected and carrier animals are an effective way to discover and eventually control the frequency of these defects within the population at large. Screening programs of this type have been used successfully in humans for many years (e.g. Tay-Sachs disease, phenylketonuria) and more recently have been applied to animals (e.g. mannosidosis in cattle; hip dysplasia, eye, blood and heart diseases in dogs). Genetic screening may be essential to the survival of breeds in which mild or moderately severe defects have been propagated unknowingly for many generations.

It is important that the top-producing sires and foundation dams of a breed be screened for conditions prevalent in that breed or in the species generally, because they represent the major nucleus of genetic material for the current and future decades. Most purebred animals raised today have evolved over the years from a relatively small gene pool. Even though a particular genetic disorder may initially have been recognized in a specific line or family within a breed, all important breeding stock of the breed need to be screened because their similar genotype evolved from the original restricted gene pool. If this approach is not taken, the frequency of genetic defects in the breed will inevitably increase and have a negative impact on overall health and longevity.

Depending on the mode of inheritance, different approaches may need to be applied for the detection and control of genetic disorders. It is advantageous to be able to select against heterozygotes (carriers) rather than have to eliminate affected individuals from a breeding program once the condition is manifested. Control and elimination of the disease by testing are feasible and reliable in cases where the asymptomatic or carrier state has an expressed phenotypic, biochemical marker (e.g., as measured in a blood, urine or saliva test, electrocardiogram, skin biopsy, eye examination, or hair analysis). Some current examples include testing for bleeding disorders like von Willebrand disease and hemophilia; autoimmune thyroid disease leading to hypothyroidism; the various eye, heart, metabolic enzyme and storage disorders; and the bone and neuromuscular diseases. Coupled with this approach to eliminating undesirable traits is the necessity to evaluate breeding stock regularly for overall soundness, reproductive health and performance, and longevity.

Features Related to Genetic and Other Data Associated with Animals

A. Physical Characteristics of Disease

In the early days when animal breeders began recognizing recurring symptoms of disease states or physical characteristics, the undesirable features of these traits led them to select away from the problems by test mating and eliminating affected animals from the breeding pool. While this remains one way to select against inherited and congenital diseases, more reliable approaches have been implemented by screening for biochemical markers and most recently by using molecular genetic techniques.

A comprehensive worldwide database contains the following information for individual purebred animals:

Host characteristics: age, sex, neuter status, pedigree, height, weight, body mass index, coloration and markings, eye color, etc.

Diet: type and amount of dog and human foods consumed, vitamin and mineral supplements, frequency of feeding. This is used to derive the percentage of calories derived from fat, carbohydrate, and protein.

Medical history: occurrence of diseases, infections, etc., including date of onset, treatment, duration, and outcome, cause of death and method of diagnosis; type and amount of medications used for treatment or prevention of disease; type and frequency of vaccinations.

Personality and temperament: based on previously used personality scales.

Laboratory data: consists of routinely collected blood, serum chemistry tests, urinalysis, etc., as well as laboratory tests performed to screen for or diagnose specific conditions such as immune-mediated thyroiditis, hypothyroidism, cancer, etc.

Special diagnostic test results: include tests for hip dysplasia, congenital eye diseases, congenital heart diseases, blood disorders, and other suspected inherited disorders as tests become available.

Genetic information: derived from the canine genome project as well as tests for specific inherited conditions such as progressive retinal atrophy, hemophilia, and von Willebrand disease.

B. Phenotypic Markers of Disease

While animal breeders (e.g., of purebred dogs) for the most part have endorsed the long standing genetic screening programs for hip dysplasia and blood and eye diseases, emphasis on other genetic disorders has arisen, now that the major infectious, parasitic, nutritional and traumatic diseases have been addressed and controlled to a large extent by modem veterinary medical practice. Furthermore, most animal fanciers become involved in breeding and showing their animals as a hobby rather than a prosperous enterprise as might apply to livestock or the performance racing industry. The intense commitment to this hobby with its attendant social praise for the successful breeder and exhibitor, poses ethical dilemmas when prize-winning animals are identified as carriers of a particular genetic disorder.

For about three decades, veterinary and comparative geneticists have developed and relied upon physical and biochemical markers of specific genetic traits to identify carrier and affected animals. These methods aimed to produce reliable, practical, and affordable tests that would be predictive of the gene product, and therefore the genotype of a particular genetic disorder. To be considered accurate and predictive, retrospective analyses of data developed from these testing programs were compared to the pedigrees of animals being screened as a means of validating the tests. Such genetic screening tests would be considered reliable if they correctly identified animals as having the normal and abnormal genotypes at least 80% of the time.

An important indicator of overall health of an individual animal or breed is longevity. Relationships between a specific health-related condition and an animal's genetic, environmental influences and lifespan have been characterized, in part, for several important diseases of dogs including bone cancer (osteosarcoma) and gastric dilatation-volvulus (GDV).

Osteosarcoma: The risk of osteosarcoma increases with increasing age, increasing weight and increasing height. Compared with the German shepherd breed, the highest risk of osteosarcoma occurs among large and giant breeds, while small breeds have reduced risk. Furthermore, the risk of osteosarcoma is increased two-fold in neutered dogs.

GDV: Factors that increase the risk of GDV in purebred dogs are male gender, being underweight, eating only one meal per day, eating rapidly, and a fearful temperament. Factors that decrease the risk of GDV include a happy temperament and inclusion of table foods in the diet. The lifetime risk of developing GDV in large and giant breed dogs is 20% and 23%, respectively, whereas the lifetime risk of dying of GDV for these breeds is 6%.

Similarly, the comparative longevity of different dog breeds has been described using the age of death and other descriptive characteristics of more than 38,000 dogs that were included in a large veterinary database. Predictable relationships were found between the breed and size of dogs and the average age of death. It was noted that dogs are unique among animal species in having a more than 50-fold difference in adult body size and a corresponding large difference in longevity between the smallest and biggest dog breeds. Since these dog breeds have more than 99% of their genome in common, it suggests that the genetic code for both size and longevity is contained within a very small part of the dog's genome. As mapping of the canine genome progresses, it should be possible to identify not only genes that code for specific diseases such as cancer and GDV, but also for the genes that determine body size and longevity.

C. Genotypic Markers of Disease

Recent advances in molecular genetics have focused on mapping the human genome, and this has stimulated interest in developing parallel genetic maps for animals. For example, it is estimated that a minimum of ten years and several million dollars will be needed to map the canine genome. Once developed, a genetic map provides information about the relative order and placement of genes or specific DNA markers on specific chromosomes. This allows one to locate specific regions on chromosomes where genes of interest are likely to be found. Once a molecular marker is identified close to a specific gene of interest, screening tests for this particular marker can be used to identify individuals carrying or expressing the trait.

Other information in relation to genetic screening and health assessment is contained in the literature references listed at the end of the specification. The contents of these materials are incorporated by reference herein.

Some of the characteristics of animals with which this invention is concerned are the following:

| Animal Characteristics | Mostly Phenotype | Mostly Genotype | Genotype & Some Phenotype (Gene Product) |
|---|---|---|---|
| Species | | | X |
| Purebred | | | X |
| Crossbred | X | | |
| Mixed breed | X | | |
| Size | X | | |
| Weight | X | | |
| Age | X | | |
| Sex | | | X |
| Lifespan | | | X |
| Body type | X | | |
| Color | | | X |
| Family history | | X | |
| DNA testing | | X | |
| Genomic mapping | | X | |
| Bloodtype | | X | |
| Thyroid function | X | | |
| von Willebrand factor | | | X |
| Hemophilia | | | X |
| Other bleeding disorders | X | | |
| Glucose | X | | |
| Cholesterol | X | | |
| Alkaline phosphatase | X | | |
| Alanine aminotransferase | X | | |
| Bile acids | X | | |
| Cortisol | X | | |
| Cataracts | X | | |
| Progressive retinal atrophy | | | X |
| Microophthahnia | | | X |
| Dry eye (KCS) | X | | |
| Hip dysplasia | X | | |
| Arthritis | X | | |
| Temperament | X | | |
| Ruptured cruciate ligament | X | | |
| Hemolytic anemia | X | | |
| Urinalysis | X | | |
| Kidney stones | | | X |
| Bloat (gastric dilatation) | | | X |
| Pyoderma | X | | |
| Seborrhea | X | | |
| Sebaceous adenitis | | | X |
| Umbilical hernia | X | | |
| Inguinal hemia | X | | |
| Epilepsy | | | X |
| Heartworm disease | X | | |
| Cardiomyopathy | X | | |
| Patent ductus arteriosus | | | X |
| Immunoglobulin levels | X | | |

In the category of genotype and some phenotype, the phenotype component (measurable gene product) is typically less than 20%.

Diagnostic Testing

The development of one or more assays or techniques for performing the invented testing protocols, standards and procedures of the present invention is straightforward, and within the knowledge of a person skilled in the art. The contents of U.S. Pat. No. 5,830,7009 (Benson) entitled "Detection Method for Homologous Portions of a Class of Substances" is indicative of some of the tests and formats that are possible. The contents of that patent are incorporated by reference herein.

One or more of a panel of tests relate to at least one of endocrine function, immunologic function, gastrointestinal function and nutritional analysis, inborn errors of metabolism, paternity, DNA fingerprinting, hemostasis and coagulation function, vaccinal antibody status, adverse and potential adverse vaccine reaction, infectious diseases, pathology, blood typing and bone marrow analysis, cell cytotoxicity, cytokines and allergy testing, and markers of neoplastic or paraneoplastic change. These data are relevant to the likely morbidity, likely longevity, and/or the potential risk for disease or disorder for the animal.

The following are some examples of diseases, disorders, and physiologic states that use one or more of the diagnostic test panels set out below:

EXAMPLES

Example 1

Temperament and Longevity

Characteristics related to the temperament of the animal which impacts on its longevity are determined. Biological laboratory test data from a bodily fluid or tissue of an animal are analyzed. Such test data relate to the level of neurotransmitter activity of the animal. The data relate to at least one of the value of serotonin, the gamma-aminobutyric acid (GABA), the glutamate, the dopamine, the glycine, the aspartate, the acetylcholine, the norepinephrine, the histamine, the substance P, the vasopressin, the vasoactive intestinal peptide, the neurotensin, or the other neuropeptides of the animal. The value should fall within predetermined levels as a predictive determinant of the animal's temperament (passivity, assertiveness, or aggressivity).

Methods for measuring neurotransmitters are well known in the art. Neurotransmitters such as serotonin, epinephrine, norepinephrine, glutamate, and GABA can be measured by standard immunochemical techniques involving commercially available antibodies, either polyclonal or monoclonal. Such antibodies are commercially available from sources such as Sigma Chemical Company (St. Louis, Mo.). These immunochemical techniques can involve either radioimmunoassay or other well-established assay techniques, such as ELISA (enzyme-linked immunosorbent assay). These neurotransmitters can also be measured by standard non-immunochemical techniques such as gas chromatography. Neuropeptide neurotransmitters are preferably measured by immunochemical techniques.

Test panels Nos. 1, 2, 3, 8 and 10 set out below can be used to obtain data for this Example 1.

Example 2

Immune Stimulation and Cellular Inflammatory Response

Characteristics related to at least one of the immune stimulation reaction, evidence of neoplastic or paraneoplastic change, or the cellular inflammatory response of the animal are determined. Biological laboratory test data from a bodily fluid or tissue of an animal are analyzed. The test data relates to at least one of cell cytotoxicity markers, cytokine and chemokine levels, immunoglobulin levels, type and amount of lymphocyte subsets and lymphocyte markers, and markers of neoplastic or paraneoplastic change of the animal. The value should fall within predetermined levels as a determinant of the immune stimulation reaction, neoplastic or paraneoplastic change, or the cellular inflammatory response.

Methods for measuring lymphokines and other cytokines are well known in the art. These compounds are typically measured by immunochemical techniques using commercially available monoclonal antibodies or other methods.

Test panels Nos. 1, 3, 4, 8, 9 and 10 set out below can be used to obtain data for this Example 2.

Example 3

Inherited Organ Dysfunction or Dysplasia

Characteristics related to inherited organ dysfunction or dysplasia of the animal, at least one of which is neuronal, neuromuscular or renal are determined. Biological laboratory test data from a bodily fluid or tissue of an animal are analyzed. The test data relate to an amino acid, carbohydrate, lipid or other metabolic component, body fluid or tissue marker of the animal. The data includes obtaining data related to at least one of the value of the methyl malonic acid, the fucose-containing cell metabolites, blood or urine urate or uric acid metabolites, normoglycemic glycosuria, mannosidase containing cell metabolites, amino acid uria, amyloid deposition in tissues, neuronal ceroid lipofuscin deposition, and deposition of gangliosides and other lysomal storage substrates of the animal. The value should fall within predetermined levels as a determinant of the inherited organ dysfunction or dysplasia.

Test panels Nos. 1, 3, 5, 9 and 10 set out below can be used to obtain data for this Example 3.

Example 4

Autoimmune Thyroiditis

Characteristics related to autoimmune thyroiditis of the animal are determined. Biological laboratory test data from a bodily fluid or tissue of an animal are analyzed. The test data relate to a genetic marker for automimmune thyroiditis of the animal. The data relates to at least one of the results of a comprehensive thyroid antibody test profile, DNA fingerprint (the gene map), and markers for immunoglobulin receptors on B-cells, T-cell receptors, and protein products of the major histocompatibility complex (MHC) genes (Class I and II allellic HLA, DLA or equivalent antigenic specificities of the animal. Test assays to screen for MHC genes include restriction fragment length polymorphism (RFLP), polymerase chain reaction (PCR) RFLP, PCR sequence-specific oligonucleotides (SSO) and PCR sequence-specific primers (SSP). The value(s) should fall within predetermined levels as a determinant of autoimmune thyroiditis.

Test panels Nos. 1, 2, 3 and 10 set out below can be used to obtain data for this Example 4.

Example 5

Mammary Cancer

Characteristics related to presence of or susceptibility to mammary cancer of the animal are determined. Biological laboratory test data from a bodily fluid or tissue of an animal are analyzed. The test data relate to estrogen (estradiol-17β), estrogen receptors, interleukin (IL) 6, progesterone, and progesterone receptors. The value should fall within predetermined levels as a determinant of the presence of or susceptibility to mammary cancer.

Test panels Nos. 1, 2, 3 and 10 set out below can be used to obtain data for this Example 5.

Example 6

Immune Surveillance

Characteristics related to the tissue environment of the eye and brain (ocular and blood-brain barrier) which are sites protected from the normal immunologic surveillance mechanisms are determined. Biological laboratory test data from a bodily fluid or tissue of an animal are analyzed. The test data relate to the soluble and cellular immune inflammatory response mediators (cytokine and chemokine levels, immunoglobulin levels, and lymphycyte susbset markers). The value should fall within predetermined levels as a determinant of integrity of protected immune surveillance mechanisms.

Test panels Nos. 1, 3, 5, 6, 8, 9 and 10 set out below can be used to obtain data for this Example 6.

Example 7

Inherited Bleeding Disorders

Characteristics related to the tendency to bleed excessively are determined. Biological laboratory test data from a bodily fluid or tissue of an animal are analyzed. The test data relate to a comprehensive assessment of the hemostatic and coagulation function. The value should fall within predetermined levels as a determinant of the presence of bleeding disorder.

Test panels Nos. 1, 7, and 9 set out below can be used to obtain data for this Example 7.

Test Panels

The following are some specific diagnostic test panels and specialized diagnostic tests and test groups used to monitor health, morbidity, mortality and longevity of animals and animal families, and to predict the potential risks of disease or disorder:

Test 1: Comprehensive Diagnostic Test Panel

Patient phenotypic descriptors and genotypic descriptors/background; complete blood count (CBC) and platelet count, platelet size, platelet morphology; serum chemistry profile [e.g., AST (SGOT), ALT (SGOT), bilirubin (total, direct and indirect), alkaline phosphatase, GGT (GGTP), total protein, albumin, globulin, A/G ratio, cholesterol, BUN, creatinine, BUN/creatinine ratio, phosphorus, calcium, corrected calcium, calcium/phosphorus ratio, glucose, amylase, lipase, sodium, potassium, Na/K ratio, chloride, CPK, triglyceride, osmolality]; complete thyroid profile (total T4, total T3, free T4 (ED or other), free T3, T3 autoantibody, T4 autoantibody, TSH, thyroglobulin autoantibody); and urinalysis, urine culture, and sensitivity, if indicated.

Test 2: Diagnostic Test Panels for Endocrine Function

Patient phenotypic descriptors and genotypic descriptors/background, plus any or all of selected tests from the following list:

1) Thyroid Function: total T4, total T3, free T4 (ED or other), free T3, T3 autoantibody, T4 autoantibody. Molecular screening for autoimmune thyroiditis including immunoglobulin receptors on B-cells, T-cell receptors, and major histocompatibilty complex (MHC) genes Class I and II allellic HLA, DLA, or equivalent animal antigenic specificities (RFLP, PCR/SSO, PCR/SSP).

2) Adrenal Function: cortisol (asal and after stimulation with ACTH, or serially after suppression with high or low-dose dexamethazone); endogenous cortisol; and endogenous ACTH.

3) Reproductive Function: testosterone; estradiol-17β; relaxin (pregnancy diagnosis); progesterone; luteinizing hormone; estrone sulfate; follicle stimulating hormone; vaginal cytology and/or culture; testicular cytology or biopsy; prostatic cytology, biopsy or wash; screens for ovarian or testicular remnants.

4) Pancreatic Function: amylase; lipase; glucose; glucagon, trypsin-like immunoreactivity (TLI); insulin, fructosamine; glycosylated hemoglobin.

5) Parathyroid Hormone Function: parathormone; ionized calcium.

6) Other Endocrine Function: aldosterone; 21 adrenal hydroxylase; vanylla mandelic acid (VMA, for epineplrine and norepinephrine metabolities).

Test 3: Diagnostic Test Panels for Immunologic Function

Patient phenotypic descriptors and genotypic descriptors/background, plus any or all of selected tests from the following list:

Antinuclear antibody (ANA)—if positive, run double stranded, single stranded, speckled, anti-RNA levels; Coombs' testing (direct and indirect; elution or microbeads gel-test); rheumatoid factor, serum electrophoresis—if abnormal, run immunoelectrophoresis, isoelectric focusing, immunoblotting (Western, Northern, Southern blots); immunoglobulin levels (IgG, IgA, IgM, IgD and IgE); complement levels (C1, C1a, C1 esterase inhibitor, C3, C4, C5–C9); LE-prep testing; lupus anticoagulant (dilute Russell's viper venom test or dilutional inhibitor test); urine protein SDS-gel electrophoresis; fibronectin and anti-fibronectin antibody; flow cytometry with fluorescence activated cell sorter (FACS, for leukocyte subsets and markers such as $CD4^+$ and $CD8^+$; leukocyte chemotaxis (leukocyte migration inhibition test, leukotrienes); cytokines including lymphokines and monokines (macrophage-derived) such as the interleukins (IL) [e.g. IL-6 regulated by estradiol-17$\beta$, IL-8 acts as neutrophil chemotactic factor], interferons, tumor necrosis factor(s), leukotrienes, colony stimulating facors, transforming growth factor-beta and chemokines (inflammatory cytokines); anti-platelet antibody tests (serum, bone marrow); anti-megakaryocyte antibody tests (IFA, elution); and anti-leukocyte antibody tests (direct and indirect anti-neutrophil cytoplasmic antibody, antilymphocyte antibody, etc.).

Test 4: Diagnostic Test Panels for Gastrointestinal Function and Nutritional Analysis Patient phenotypic descriptors and genotypic descriptors/background, plus nutritional and food supplement past and current use, plus any or all of selected tests from the following list:

Serum nutrients and vitamin analysis; CBC as in Test 1; serum chemistry as in Test 1 plus magnesium and iron; urinalysis, urine culture and sensitivity, if indicated; urine fractional excretion; serum and urine amino acid analyses; serum cobalamin (vitamin $B_{12}$) and folate analysis; TLI [same as Test 2, 4)]; fecal flotation; Giardia screen, Clostridium perfringens enterotoxin test; cryptosporidiosis test (FA); toxoplasmosis test; bile acids test (resting and postprandial); fecal alpha-$_1$ protease inhibitor activity. If any abnormalities are present, further investigation includes ion-coupled plasma emission spectroscopy (ICP) for mineral analysis, and electrophoresis.

Test 5: Diagnostic Test Panels for Inborn Errors of Metabolism

Characteristics related to presence of or susceptibility to mammary cancer of the animal are determined. Biological laboratory test data from a bodily fluid or tissue of an animal are analyzed. The test data relate to estrogen (estradiol-17$\beta$), estrogen receptors, interleukin (IL) 6, progesterone, and progesterone receptors. The value should fall within predetermined levels as a determinant of presence or susceptibility to mammary cancer.

Patient phenotypic descriptors and genotypic descriptors/background, plus any or all selected tests from the following list:

Genetic screening tests including blood and urine analyses for mucopolysaccharides, cerebrosides, glycogen-storage diseases, phenylketones, phosphofructolinase, mannosidases, combined and specific immunoglobulin deficiencies/dysfunctions; skin and tissue biopsies; karyotyping for genotype determination; and DNA marker analyses.

Test 6: Diagnostic Test Panels for Paternity Testing and DNA Fingerprinting

Patient phenotypic descriptors and genotypic descriptors/background, plus any or all selected tests from the following list:

Major histocompatibility complex (MHC) Class I and II alleles [analyses of HLA, DLA, or equivalent animal antigenic specificities]; genotyping; gene mapping and fingerprinting.

Test 7: Diagnostic Test Panels for Hemostatic and Coagulation Function

Patient phenotypic descriptors and genotypic descriptors/background, plus any or all selected tests from the following list:

Platelet count, platelet size (blood slide, mean platelet volume), platelet morphology (light, scanning, and electron microscopy); prothrombin time; partial thromboplastin time; fibrinogen; fibrin-fibrinogen degradation products (D-dimer test); platelet function tests (aggregation, release, clot retraction, whole blood aggregation, ristocetin cofactor); von Willebrand factor antigen and multimer analysis; specific coagulation factor analyses (factors II, V, VII, VII:C, IX, X, XI, XII, XIII); fibrinolytic tests (plasminogen, plasmin, antiplasmin, tissue plasminogen activator, dilute whole blood lysis test, euglobulin lysis test); anti-thrombin III test; circulating anticoagulant tests; platelet factors 3 and 4 (heparin cofactor); protein C; protein S; kinin-kinogen tests; prekallikrein test; alpha$_1$-antitrypsin assay; alpha$_2$-macroglobulin assay; $C_1$ esterase inactivator assay; anti-platelet antibody, and anti-megakaryocyte antibody tests (see Test 3).

Test 8: Diagnostic Test Panels for Vaccinal Antibody Status, and Adverse Vaccine or Potential Adverse Vaccine Reaction Patient phenotypic descriptors and genotypic descriptors/background, plus any or all selected tests from the following list:

1) Serology for Vaccinal Antibody: canine distemper, canine parvovirus, canine coronavirus, canine parainfluenza virus, infectious canine hepatitis virus, canine bordetella, canine Lyme (borrelia), canine leptospirosis, rabies virus, feline panleukopenia virus, feline leukemia virus, feline infectious peritonitis virus, feline immunodeficiency virus, feline calicivirus, feline hexpesvirus, and equine herpes viruses I–IV), etc.

2) Adverse Vaccine Reactibn: Same as Test 3, but especially CBC; ANA; Coombs' test; platelet count, size, and morphology; anti-neutrophil cytoplasmic antibody, marker for vasculitis; complement tests; leukocyte chemotaxis tests; urine protein/creatinine ratio; anti-platelet antibody; immunoglobulin levels, especially IgG, IgA, IgM; flow cytometry (FACS) leukocyte subsets; cell cytotoxicity analysis; cytokines, especially chemokines; and complete thyroid autoantibody panel.

3) Potential (High Risk) Vaccine Reaction: especially for breeds such as the Akita, Weimaraner, Standard poodle, Eskimo Dog, harlequin Great Dane; CBC; ANA; platelet count, size and morphology; complete thyroid autoantibody panel; cell cytotoxicity analysis; cytokines; and immunoglobulin levels, especially IgG, IgA, IgM;

Test 9: Diagnostic Test Panels for Infectious Diseases

Patient phenotypic descriptors and genotypic descriptors/ background, plus any or all selected tests from the following list:

1) North America: Ehrlichia species (*E. canis, E. risticii, E. equi, E. platys*, etc.); Rickettsia rickettsei (RMSF); Borrelia species (Lyme disease); Bartonella species (*B. henselae, B. vinsonii, B. clarridgeiae, B. kochlerae*); systemic fungal diseases (Coccidioides spp, Cryptococcus spp, Histoplasma spp, Blastomyces spp, Aspergillus spp, ringworm); mange mites (Demodex, Sarcoptes, Chyletiella, etc.); enteric diseases (Clostridium perfringens enterotoxin);protozoan diseases (Toxoplasma spp.; Coccidia spp; Giardia spp); retrovirses (feline leukemia virus, feline immunodeficiency virus, equine infectious anemia virus, bovine leukemia virus, caprine arthritis virus; Corona viruses (canine coronavirus, feline enteric coronavirus, feline infectious peritonitis virus; Babesia spp (*B. canis, B. gibsoni*); Dirofilaria spp (heartworm); other parasitic diseases (fleas, ticks, roundworms, tapeworms, hookworms, Strongyles and other intestinal parasites); and Chlamydia antigen (PCR testing).

2) International: Same as above plus Leishimania spp; Trypanosoma spp.; Anaplasma spp; *Yersina pestis.*

Test 10: Other Diagnostic Tests

Patient phenotypic descriptors and genotypic descxiptors/ background, plus any or all selected tests from the following list:

Pathology (anatomic, histological, cytologic, immunohistochemical, electromicroscopy, FACS); blood typing; bone marrow analysis and specific immunohistochemical staining; RFLP and PCR testing (applicable to many of the above categories); IFA and FA testing; ELISA testing, cell cytotoxicity testing, cytokine testing (see Test 3, other cytotoxic cell and mitochondrial tests); markers of neoplastic and paraneoplastic change (cancer); neurotransmitters including serotonin, the gamma-aminobutyric acid (GABA), the glutamate, the dopamine, the glycine, the aspartate, the acetylcholine, the norepinephrine, the histamine, the substance P, the vasopressin, the vasoactive intestinal peptide, the neurotensin, or the other neuropeptides; and amino acid profiling.

Overall System

FIG. 1 is an overview of the web-based system to provide access to the invented database management system. With this system multiple users, for instance, remote users 8, access the web site 4 using the Internet 6. Each of the users 8 has a computer terminal with the appropriate software for accessing Internet. The users 8 may be unknown to the web server computers 10 and 12. Each user 8 is allowed to browse the web site and explore how the system functions.

There are several aspects to maintain security of information maintained in the database server 22 and a banking system 28. A fireall 20 prevents any user 8 from accessing any of the components behind the firewall 20. In this way the users 8 have access to the web server computers 10 and 12, but only have access to the database server 22 through the firewall 20. The database server 22 maintains, among other things, various database fields with respect to each of the health profiles of subjects and the genetic information of a subject and groups. The database 22 maintains the services with a designation associated to determine what health assessment data and genetic data can be browsed by the users 8. Each of the web server computers 10 and 12 allow users 8 to view subject and group categories and actual services and data products which are available from the database.

The web server computers 10 and 12 can be identical and can be duplicated as additional load or growth on the system occurs. The web server computers 10 and 12 share the responsibility for servicing the users of the site. This arrangement provides for expandability of the system by merely adding additional web server computers as necessary.

Preferably, the system includes an appropriate computer terminal 24 for interfacing with independent financial institutions which are connected on-line via the serial connection 26 to the financial institution computers 28. This allows automatic real time confirmation of the access of health profile and genetic data services and products. Once a user requires access to a product or service, the user goes through an identification or registration process and the exchange of financial information to allow for credit or debit card payment of the purchase. This is verified, confirmed and authorized by the appropriate bank system institution 28. Confirmation of the purchase or deposit of data, or a service is made by a mail server 34 which sends an E-mail to the user 8 confirming the purchase or deposit. The mail server 34 allows for mail to be received and sent out. Security of the various databases is maintained. Alert messages are generated when an unauthorized access is attempted. Verification messages, authorization messages and confirmation messages are generated as appropriate.

The database server 22 is also designed to interact with an input computer 32 operated by a CDPR. A firewall 30 serves to prevent unauthorized access to the database server 22 or to the input computer 32. The input computer 32 can input health profile data and genetic data to the database, after appropriate access and/or passwords are entered into the system. Similarly, users 8 through their own computers can use appropriate access codes and passwords to access input data to the database server 22. This is tightly controlled for security reasons. The data may only be added to an independent sub-database of the data server 22, and only after scrutiny by the CDPR operator of the database through input computer 32, will this data from users 8 be subsequently added to the main database server 22.

Figure 2:
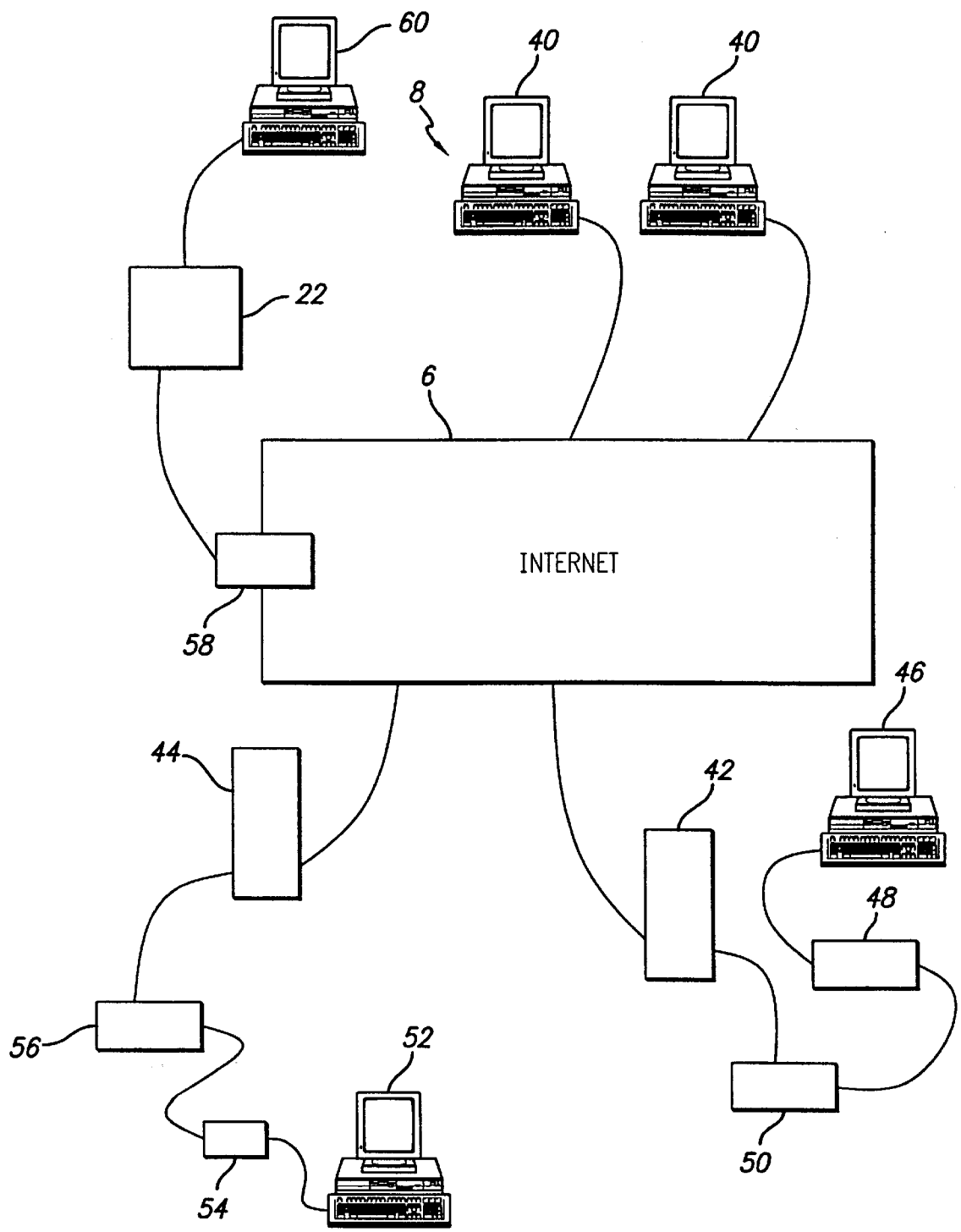
FIG. 2 is a graphical illustration of a computer network, namely the Internet.

FIG. 2 is an illustration of the Internet and its use in the system of the invention. The Internet 6 is a network of millions of interconnected computers 40 including systems owned by Internet providers 42 and information systems 44 such as America Online™. Individual or corporate users may establish connections to the Internet in several ways. A user on a home PC 46 may purchase an account through the Internet provider 42. Using a modem 48, the PC user can dial up the Internet provider to connect to a high speed modem 50 which, in turn, provides a full service connection to the Internet. A user 52 may also make a somewhat limited connection to the Internet through a system 20 that provides an Internet gateway connection 54 and 56 to its customers. The database 22 is also connected into the Internet 6 through an appropriate modem or high speed or direct interface 58. The database 22 is operable and maintained by the CDPR operator computer 60. Users of the databases of the invention would access the Internet in an appropriately selected manner.

Figure 3:
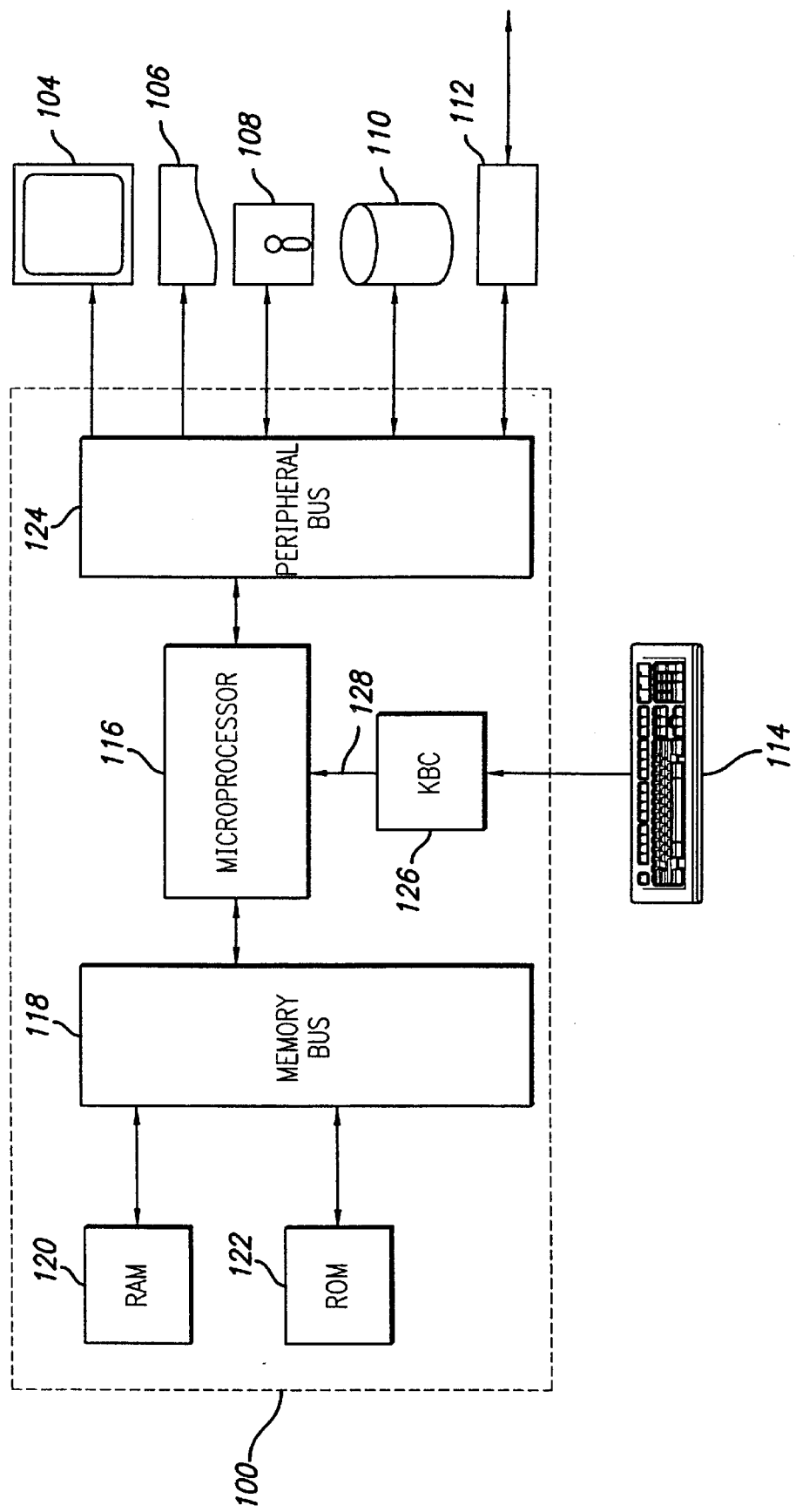
FIG. 3 is a block diagram of an exemplary computer system for practicing various aspects of the invention.

FIG. 3 is a block diagram of an exemplary computer system 100 for practicing various aspects of the invention. The computer system 100 includes a display screen or monitor 104, a printer 106, a disk drive 108, a hard disk drive 110, a network interface 112, and a keyboard 114. The computer system 100 includes a microprocessor 116, a memory bus 118, random access memory (RAM) 129, read only memory (ROM) 122, a peripheral bus 124, and a keyboard controller 126. The computer system 100 can be a personal computer, such as an Apple computer, e.g., an Apple Macintosh™, an IBM™ personal computer, or a compatible, a workstation computer, such as a Sun Microsystems™ or Hewlett-Packard™ workstation, or some other type of computer.

Microprocessor 116 is a general purpose digital processor which controls the operation of computer system 100. Microprocessor 116 can be a single-chip processor or can be implemented with multiple components. Using instructions retrieve from memory, the microprocessor 116 controls the reception and manipulation of input data and the output and display of data on output devices.

Memory bus 188 is used by the microprocessor 116 to access RAM 120 and ROM 122. RAM 129 is used by microprocessor 116 as a general storage area and as scratchpad memory, and can also be used to store input data and processed data. ROM 122 can be used to store instructions or program code followed by microprocessor 116 as well as other data.

Peripheral bus 124 is used to access the input, output, and storage devices used by computer system 10. These devices include the display screen 104, printer device 106, disk drive 108, hard disk drive 110, and network interface 112. The keyboard controller 126 is used to receive input from the keyboard 114 and send decoded symbols for each pressed key to microprocessor 116 over bus 128.

The display screen or monitor 104 is an output device that displays images of data provided by microprocessor 116 via peripheral bus 124 or provided by other components in computer system 100. The printer device 106 when operating as a printer provides an image on a sheet of paper or a similar surface. Other output devices such as a plotter, typesetter, etc. can be used in place of, or in addition to the printer device 106.

The disk drive 108 and hard disk drive 110 can be used to store various types of data. The disk drive 108 facilitates transporting such data to other computer systems, and hard disk drive 110 permits fast access to large amounts of stored data.

Microprocessor 116 together with an operating system operate to execute computer code and produce and use data. The computer code and data may reside on RAM 120, ROM 122, or hard disk drive 120. The computer code and data could also reside on a removable program medium and loaded or installed onto computer system 100 when needed. Removable program mediums include, for example, CD-ROM, PC-CARD, floppy disk and magnetic tape.

The network interface circuit 112 is used to send and receive data over a network connected to other computer systems. An interface card or similar device and appropriate software implemented by microprocessor 116 can be used to connect computer system 100 to an existing network and transfer data according to standard protocols. As such he computer system is connectable through an interface device with the Internet 6.

Keyboard 114 is used by a user to input commands and other instructions to computer system 100. Other types of user input devices can also be used in conjunction with the present invention. For example, pointing devices such as a computer mouse, a track ball, a stylus, or a tablet can be used to manipulate a pointer on a screen of a general-purpose computer.

The present invention in relation to the animal database management of data can also be embodied as computer readable code on a computer readable medium. The computer readable medium is any data storage device that can store data which can be thereafter read by a computer system. Examples of the computer readable medium include read-only memory, random-access memory, magnetic data storage devices such as diskettes, and optical data storage devices such as CD-ROMs. The computer readable medium can also be distributed over network coupled computer systems so that the computer readable code is stored and executed in a distributed fashion.

Specific System

Figure 4:
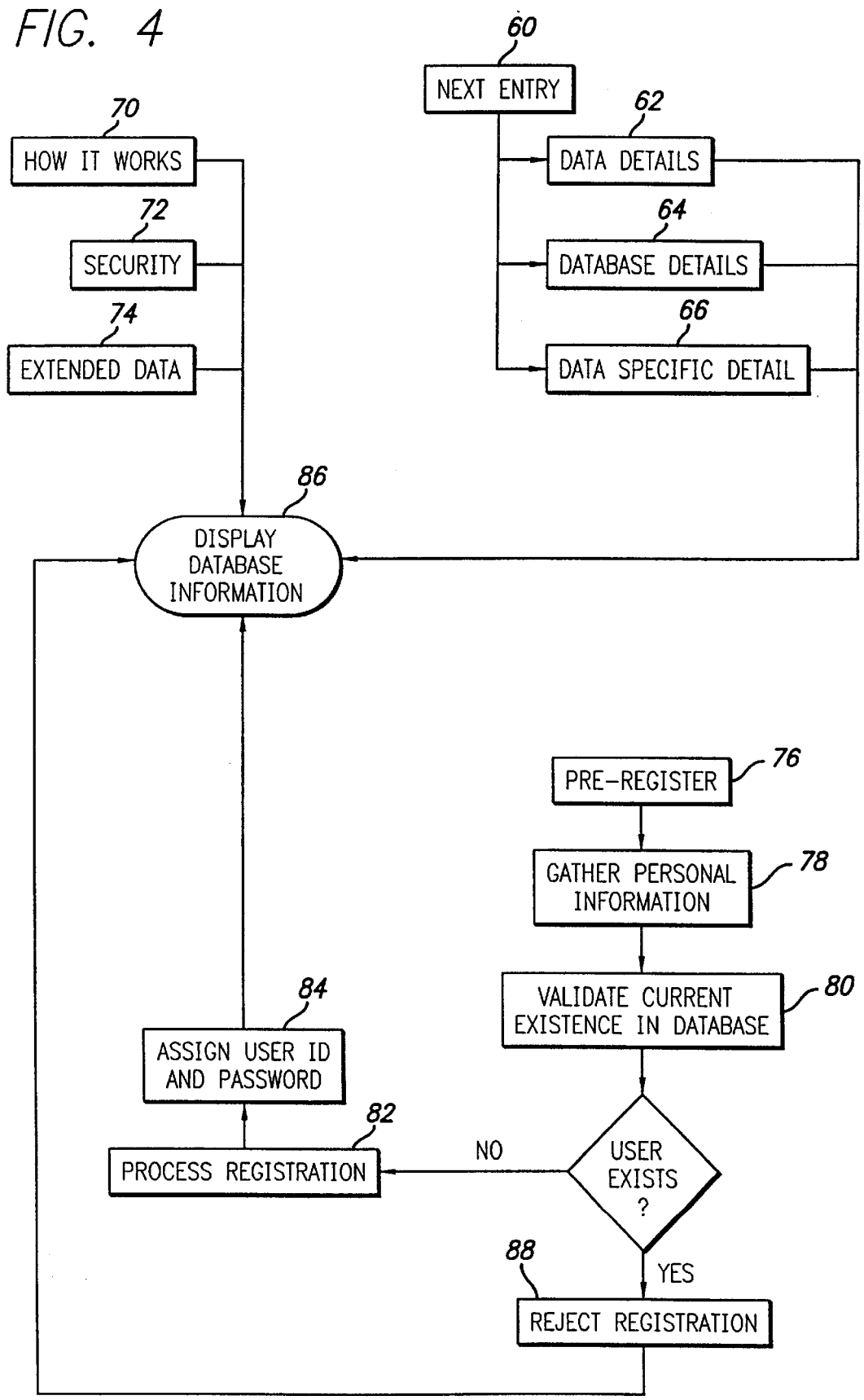
FIG. 4 is a view of a browser for the database management system for accessing an animal genetic database and a health assessment database of the invention.

FIG. 4 illustrates a browser system for use with the database system of the invention. A browser goes through a number of preliminary screens and logic steps, and reaches a screen 60 entitled "Next Entry". This screen provides data details or information generally indicated as 62. Clicking on any of these categories allows the user to review database details 64, data specific details as generally indicated by 66. In this way, the user can index through a number of screens to get information regarding the different databases of the system. In addition, clicking on any of the triggers 70, 72, 74 and 76 is possible. These correspond to HOW IT WORKS, SECURITY, EXTENDED DATA and PRE-REGISTRATION. Clicking on trigger 70 provides the user with information on how the process works, explains the system, and provides details on how the user can participate in the database and obtain data or input data. Clicking on trigger 72 provides details regarding security of the system and automatic payment. In some cases, products and services are offered with extended data and clicking on trigger 74 which can provide details of the extended data and explains that this may only be available on certain services or products.

Trigger 76 allows a user to pre-register and obtain user ID number. This ID number is combined with financial information retained in the database in an encrypted form. The pre-registration trigger 76 follows with step 78 which is to gather personal information such as credit card number and expiry date to allow for automatic payment. Step 80 is to validate a current existence in the database, if this occurs. With a negative answer, the user is directed into a registration process indicate as 82. A user ID is assigned and a password is entered. This information is maintained in a portion of the database 22. At 84 the user is provided a screen identifying the user ID at screen 86. If the user already exists, the registration process is rejected at 88 and the user is advised of the information at the display 86. The screen at 86 would also represent the information which is available in the database 22.

Figure 5:
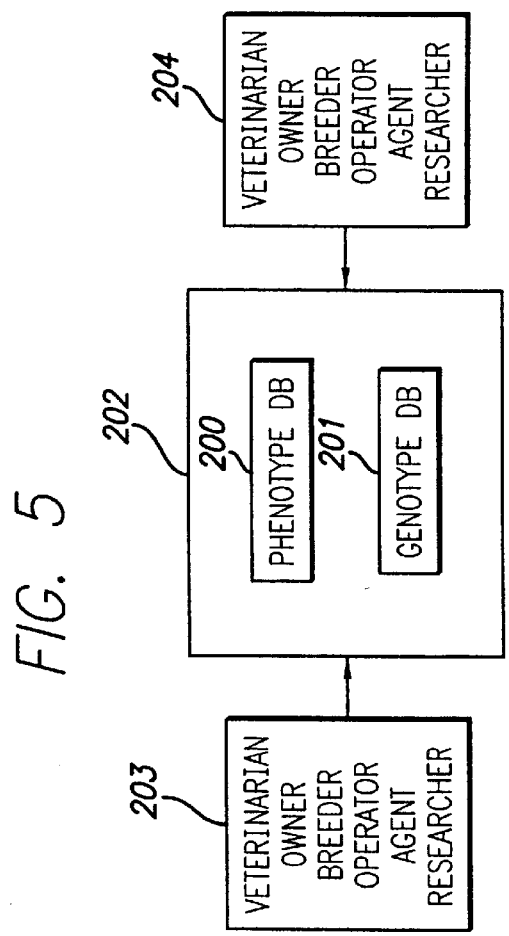
FIG. 5 is a basic flow diagram illustrating an exemplary process by which an operator of a CDPR receives and transmits data relating to health assessment and genetic information.

In FIG. 5 there is shown a basic block diagram of the components making up the CDPR. There is the phenotype database or physical health database 200 and a genotype database or genetic information database 201. These are contained in part of the overall CDPR database 202. User input 203 can be obtained from a remote user such as a veterinarian, owner, breeder, or the operator of the database, an agent or researcher. The output from the database 204 could be to the veterinarian, owner, breeder, operator, agent or researcher.

Figure 6:
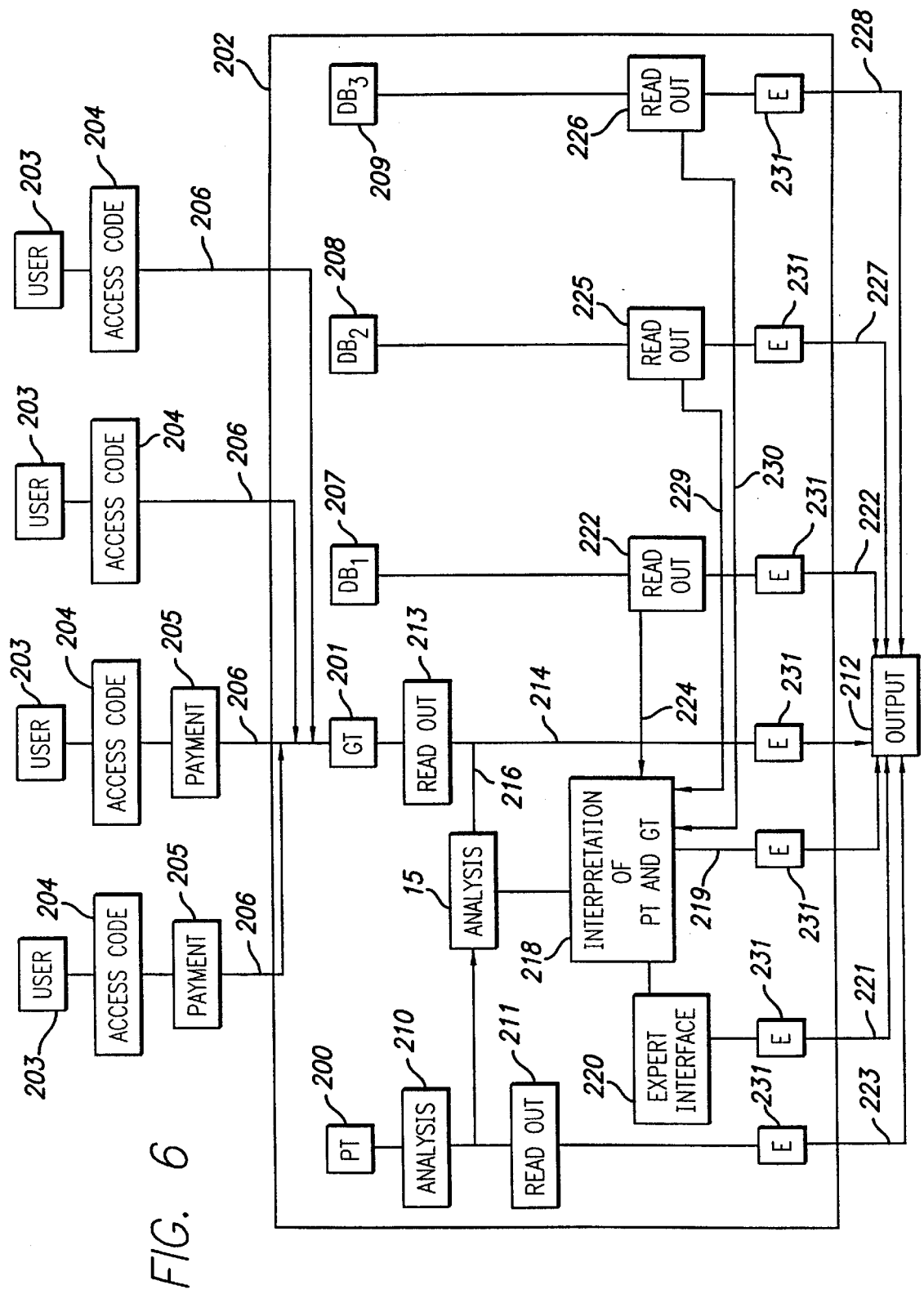
FIG. 6 is a detailed flow diagram of the system steps employed in one embodiment of the present invention wherein a remote user accesses and outputs data.

FIG. 6 shows a relationship for retrieving data from the database 202. The user 8 is represented here as a veterinarian, owner, breeder, operator, or researcher 203 who accesses the CDPR 202 accesses a first screen through a computer network 6 which inquires about information about the user. An access request message is sent, and an appropriate access enabling message is transmitted. The user 203 can obtain partial or full access to the CDPR 202 according to the scale of authority given to the user 203 to access data. There is a computer program system 205 to ensure that payment is made as appropriate before access to the CDPR 202 is granted. In some situations, the appropriate access code 204 can permit bypassing the payment requirement 205 as indicated by line 206. Payments 205 through the computer program can be effected by a credit card entry and automatic transfer to a financial institution on behalf of the operator of the CDPR 202. Such payment for access to the database is effected by a system which is well known in the art. The financial institution will appropriately credit the operator of the CDPR 202 in a financial manner as established between the operator and the financial institution.

Within the CDPR 201 there is the ability to access the physical health phenotype database 200, the genotype database 201, and other databases 207, 208 and 209, respectively. The phenotypic and genotypic information together with other database information can be presented on a single screen or monitor or other viewing means, for instance, hard copy format. The access therefore can be to multiple databases contained within the CDPR 202. After accessing the physical health database 200, the user obtains an analysis report from module 210. The user is then able to read the analysis as indicated by 211 and output the analysis from the read-out 211 as indicated by output 212. The output 212 can be a computer screen read-out, fax or voice information.

The physical health or phenotype database 200 is subject or group specific. In other words, the data obtained in that database is specific to a particular animal or animal group (breed, family, species, etc.) which has been the subject of a laboratory or research biological examination such that fluid or tissue samples have been subject to analysis in one or more laboratory or research environments. These biological reports can include those from specimens of blood, urine, other body fluids, skin, eyes, skeletal and other tissues. The PT database 200 has the ability to store the subject specific information as required within the CDPR 202.

The genotype specific or genetic disorder or disease data is retained in the database 201 within the CDPR database 202. This data is either subject specific, family specific, breed specific, species specific, disorder specific, or disease specific, and is group or subject specific. The user can access the genotype database 201 and obtain a read-out 213 which can then be transmitted along line 214 to an output 212 in the same manner that the physical health assessment is obtained as an output.

In an alternative approach, the reader can request an analysis 215 from the genotype database as indicated by line 216. This analysis can receive data along line 217 from the analysis information of the physical health assessment. Interpretation of the PT and GT can be obtained as indicated by 218, and this can then be outputted as indicated along line 219. The interpretation of PT and GT 218 can be performed by an algorithm relating to the coefficients and predictability of information relating to disorders, disease and longevity when considering the data from the two databases PT 200 and GT 201. This can be done automatically and outputted along line 219, or there can be an expert interface 220 using skilled personnel to interpret the data of block 218, and this can, in turn, be outputted along line 221 to the output 212.

Database 207 can be a genetic marker database, and the information from that database can be directly input into the output through a read-out 222 and 223 to the output 212. Alternatively, the data from database 207 can be added to the interpretation section 218 of the physical health and genetic information by directing the data along line 224. This data can then be made the subject of the output along the line 219 and 221 as required.

Similarly other databases 208, 209, respectively, have read-outs 225 and 226 which can be directly coupled along lines 227 and 228 to the output, or can be directed optionally along lines 229 and 230 to the interpretation module 218. It can then be the subject of interpretation for an expert interface 220 review which is, in turn, made the subject of the output 219 and 221.

In each of the output lines 219, 221, 222, 223, 227, 228, and 214 there is also provided an encryption program 231 which can be optionally used in the system. The output 212 can include paper, electronic, or voice read-out as is required.

In this manner, the output 212 provides a compilation which combines the physical health and genetic information relating to a subject, the breed, disease, disorder and lifespan, thereby enabling the receiver of the output 212 to use the compiled information in a manner to facilitate breeding criteria which can be important in relation to animals which are usually inbred or line bred. The information can also be used to facilitate on-going monitoring of particular subject animals. The data from this system can be used to manipulate and regulate breeding, health, and longevity effectively among animals.

Figure 7:
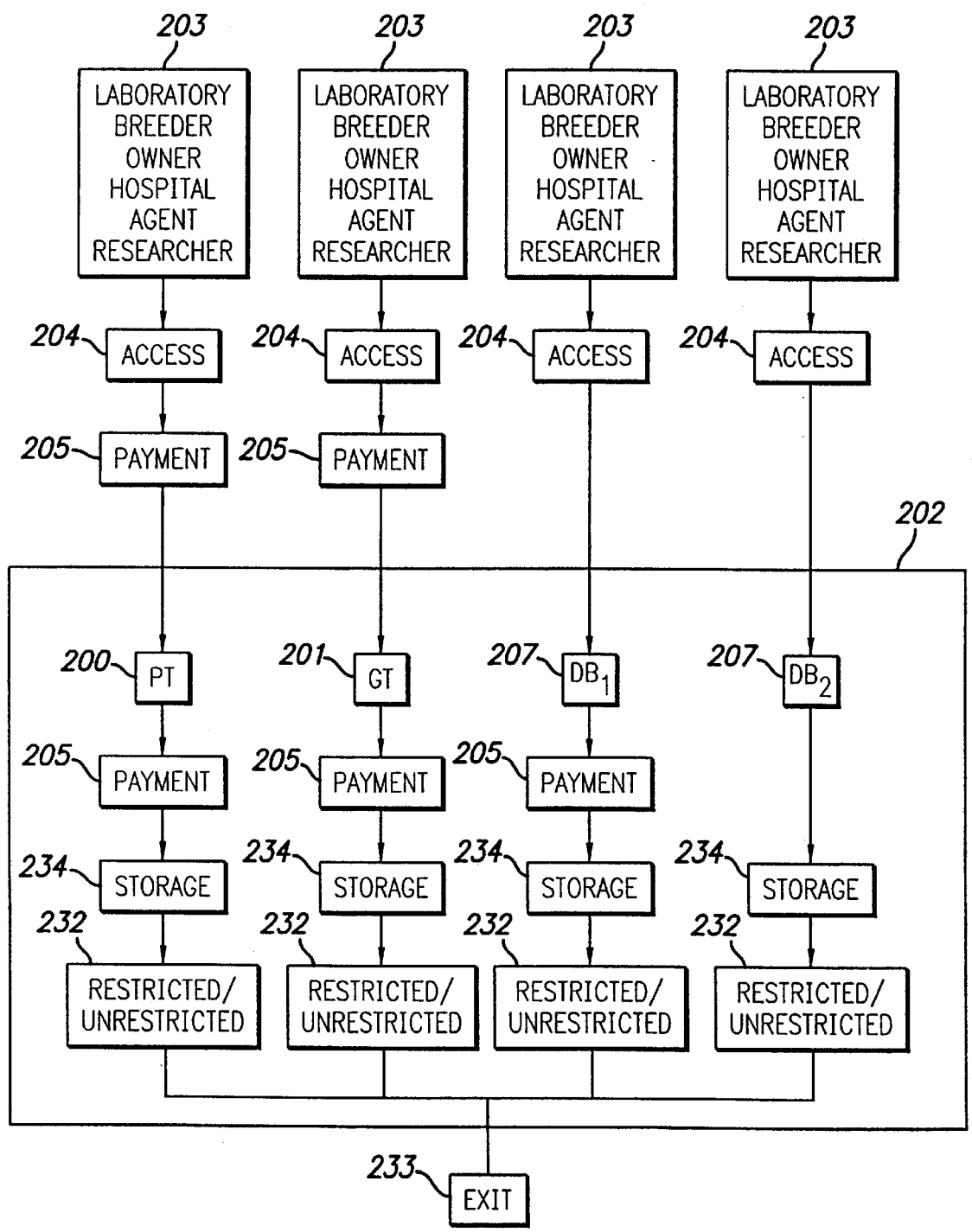
FIG. 7 is a detailed flow diagram of the methods and steps employed by a remote user to add data to the database.

The system of the invention is further described with regard to FIG. 7 which is a system for inputting data to the CDPR 202. Here multiple users 203, which can be a remote user such as a laboratory, a breeder. an owner, hospital, agent, or an operator of the CDPR 202 accesses the system through module 204 which, in turn, accesses the CDPR 202. Appropriate access request and access enable messages are sent. Within the CDPR 202 there is a physical health or phenotype module 200, a genetic or genotype data module 201, and other database modules 207, etc. After accessing the CDPR 202, additional data can be added to the modules 200, 201, 207, etc. through any of the users 203, if authorized. Depositing data into each of the modules 200, 201 and 207 can optionally require the payment to the operator of the CDPR 202 as is indicated by block 205. This system can function in the same manner as the retrieval of data from CDPR 202.

The stored data in each of the blocks 200, 201, and 207 can be set up as indicated by block 232 in a manner which is restricted or unrestricted to selected users 203. This may be necessary according to the protocols governing the inputted data to the different databases. In some cases, the waiving of deposit fees is made in the interest of freedom of the database to subsequent users who wish to retrieve data from the database. After storage of the data as indicated by block 234, the user 203 exits CDPR 202 as indicated by block 233.

As is apparent, the physical health or phenotype profile of subject animals is dynamic and grows as more data is added into the system. Likewise, the genetic genotype database also grows as increasing research of particular subjects, breeds, and the like is obtained. The deposit of new information into the CDPR 202 is regulated in a manner that the data cannot distort the databases 202 in an in appropriate manner. Likewise, users 203 cannot access the secured databases within CDPR 202 in an inappropriate manner.

Different algorithms regulate the relationship between the health profile, the genetic data, and other data relating to animals. These algorithms determine the probabilities, possibilities, and likelihood of disorders and disease in subject animals and offspring animals. They are used as predictors of the future evolvement of health of the animal. Exampt of Inter-Relationship and Algorithm Inter-Relationship of the Phenotype and Genotype Data Bases In one example the genetic influence on behavior and behavioral disorders accounts for less than half of the phenotypic expression of behavior and behavioral differences. However, behavior is the most complex phenotype, because it reflects not only the functioning of the whole being but also is dynamic and changes in response to environmental influences. These results are most dramatically seen in purebred animals because they have been inbred and line-bred to select for a particular behavior and conformation, even though the genotype of purebred breeds shows almost no variation over 100 years. Examples of this are all the different purebred dog breeds which currently exist, and have widely disparate size, weight, temperament and lifespans.

Accordingly, if the results of a mostly phenotypic database indicate abnormal thyroid function, then by relating this to the mostly genotypic and combined database categories of breed, age and sex, it is possible to determine whether the subject has or does not have heritable thyroid disease, or is likely to develop this condition within a predicted period of time.

Similarly, if the phenotypic database indicates elevated blood and urine glucose levels, then by relating this to the genotypic and combined database categories of weight, age, sex, breed and reproductive history, it is possible to determine that the subject has diabetes that is likely to be of an heritable basis.

Another example relates the phenotypic database indicating low blood von Willebrand factor level to the genotypic and combined database categories of breed, age, sex, and clinical and family history, whereby it is possible to determine whether the subject has the inherited or acquired form of von Willebrand disease.

Analyzing the data from the CDPR 102 in the manner of the present invention permits for genetic screening, health assessment profiling, and the diagnostic, prophylactic, and therapeutic management of animals.

An exemplary server performs all the operations of a conventional database system and performs additional operations in accordance with the present invention as has been discussed. The server includes a central processing unit (CPU) together with associated memory for processing information about different animals species and history. The inquiries concern animals species and history and inquiries and requests for health profiling and genetic information, and providing health profiles and genetic information. The CPU is coupled to the database and to users via a communications port. The CPU is also coupled to an electronic mail processor for processing and storing (in a storage device) e-mail messages transmitted between the CPU and various agents, users and the like. The CPU is further coupled to a data storage device. A data storage device may include a variety of the databases. The system permits for the requesting, storing and providing of data with respect to animal phenotypic information and genetic information. The format and content of the databases have been discussed in detail.

Figure 8:
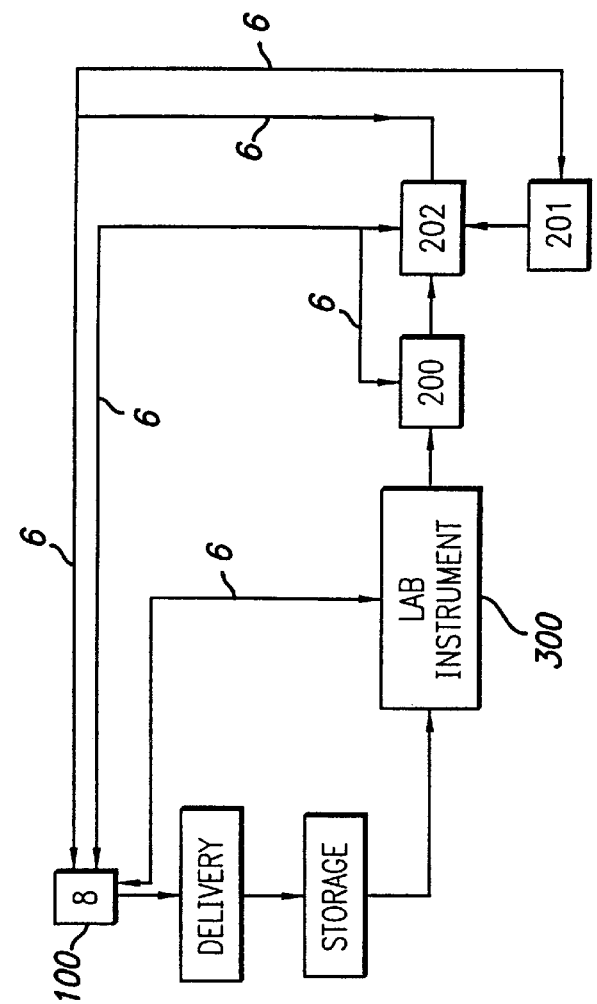
FIG. 8 is a flow chart illustrating an exemplary process by which the laboratory dynamically contributes, transmits and receives data associated with health assessment and genetic data to the CDPR.

FIG. 8 presents an overview of the laboratory instruments apparatus, system, and method operable with the present invention in relation to a CDPR 202. The present invention allows access by remote users with computers or processors 100 to receive and access data on specimens. Using the Internet 6 or other computer network or communication link capability, the remote user 8 sends a message to request access to the services provided by the laboratory or operator which has a CDPR 202. If access to the CDPR 202 is granted, a message is sent to the remote user computers 100. This message includes instructions enabling the remote user 8 to define and access data stored in the CDPR 202.

In one form of the invention, the desired data is based on the submission of test specimens of a specific animal to the laboratory. In some other cases health profile test data 200 can be inputted into the CDPR 202 having the genetic database 201. The CDPR 202 can perform an analysis and correlation between the health profile database 200 and the genetic database 201.

Using the communications link, the remote user 8 communicates with the laboratory or the CDPR 202. Specimens can be packaged and physically transported to the laboratory site via commercially available common carriers, such as the postal service or courier services. When the packages arrive, the laboratory places them in storage, or the tests are performed. Instruments 300 perform the tests to obtain data as specified by the remote user 8. The biohazardous samples can be disposed of a waste material. The test results, or output is provided as part of a health profile database 200 of the CDPR 202 and is available to the remote user 8.

If desired, the remote user 8 can arrange to have the data stored in the CDPR 202, made available to other remote users 8. The remote user 8 can also request the laboratory to perform analysis on the health profile data 200 generated.

In one embodiment, the communications link is a computer network and the message transfer modality is, for instance, the Internet 6, and/or an Intranet and/or an Extranet. The network systems are particularly suited to the application described herein since it offers global or widespread accessibility and high speed data transfer of large amounts of information.

A security unit allows remote users to designate who has permission to view or use their data. Feasible options for these information management requirements include: access by the submitting remote users only, access by certain designated researchers and collaborators, timeembargoed data followed by wider access, and unrestricted access by all. A commerce unit can implement functions related to the business aspects of the CDPR facility, including billing, inventory management of support materials.

A multimedia unit comprises means to store, manipulate, and present audio, graphical, video information. This information may include a video explaining how the CDPR is used, a visual depiction of the data, methodology, or a comment regarding the background of the data. The multimedia unit may also implement subscription functions, so that updated data automatically provided to remote users or other interested parties.

The operations performed by the present invention begins when the controller receives an access request message from the remote user via a communication link. Using information in the access request message and any other available information, the controller determines if the remote user is authorized to access the CDPR 202. If so, an access enabling message is transmitted from the controller to the remote user 8. The access enabling message can comprise a set of computer instructions transmitted over the Internet 6 which is downloaded into the remote user memory for execution by the remote user processor. These instructions may be enabling, that is, they may allow direct communication between the remote user 8 and the CDPR 202 with no further need for the controller. In another embodiment, the access enabling message may simply comprise a password or other enabling message which allows the remote user 8 to proceed. The remote user 8 can access or submit data to the CDPR 202 according to different protocols and regimes and security arrangements.

CONCLUSION

As is clear the tests above which relate to at least one of endocrine function, immunologic function, gastrointestinal function and nutritional analysis, metobolism, paternity, DNA fingerprinting, hemostasis and coagulation function, vaccinal antibody status, adverse vaccine reaction, infectious disease, pathology, anatomic, histological, cytologic, immunohistochemical, electromicroscopy, FACS, blood typing, bone marrow analysis and immunohistochemical staining, and allergy reaction about the animal provide usefull information. This is in a manner previously not obtained.

As the above demonstrates, there is a need for providing data analysis and dissemination services to a wide variety of globally-distributed remote users. There is a need for providing a system for inputting, storing and retrieving data related to animal health assessment and genetics in a manner which permits for the effective use of this information.

The system also permits for the access to the genetic and/or phenotype data through a password and a system whereby access to the data generates a fee. This system permits for the access or to provide data with regard to credit cards or the like to ensure that the fee is transmitted automatically to a banking system for the account of the database when such data is accessed.

This system also provides for a situation wherein payments can be made by credit card for requests to perform health assessment profiles and secure genomic mapping and genetic screening information. Such bioinformatics system can also permit for the automatic payment for such services and products to the banking system of the database or laboratory. As such, the database may require that the payments be guaranteed, for instance by supplying a credit card number with a request for performance of services and a product, and for the retrieval of such data.

A user can submit a request to the database in any number of ways. For example, the request can be submitted via on-line direct connection, namely through a computer network such as the Internet. An intermediate researcher such as a veterinarian or scientist other than the owner could also submit the request on behalf of the owner using the e-mail capabilities of the central database system. Alternatively, the user can submit the data via an interactive voice response unit coupled to the database system of the supplier. In some situations, the database supplier can decide whether to supply the health assessment information and/or genomic mapping and genetic screening information based on the criteria of the user or its intermediary agent. Such user or intermediary agent can be notified of the decision via the interactive response unit or a live operator.

The user or agent can log into the database system and obtain the necessary records relating to an animal physical health and/or genetic ancestry or offspring. The database system can transmit in real time or on a periodic basis as determined, thereby, providing information regarding the health assessment or the genetic background and forward this information to the user and/or its intermediary agent.

The data storage devices of the invention include a variety of databases including a database relating to the phenotypic data of a particular species, a database relating to health assessment or other phenotypic data of particular animals in a particular species, and genetic characteristics of different species and different family trees relating to different species. The family trees would contain information including the origin, genomic map, and parental lines of a species and records of health and performance of a species. These databases are interrelated in an analytical manner and in accordance with different algorithms of permutations and probabilities to facilitate useful output information based on the combination of data in the genotypic and the phenotypic databases, and the selected databases.

Many other examples of the invention exist, each differing from others in matters of detail only. The invention is to be determined solely by the following claims.

REFERENCES

Dodds, W. J. More Bumps on the Vaccine Road. Adv. Vet. Med. 41:715–732, 1999.
Canine Health Conference 1997, National Parent Club of American Kennel Club/AKC Canine Health Foundation. Can. Pract. 23(1):1–56, 1998.
Ru, G, Terracini, B, Glickman, L. Host Related Risk Factors for Canine Osteosarcoma. Vet. J. 156:31–39, 1998.
Glickman, L, Glickman, N, Schellenberg, D, et al. Multiple Risk Factors for the Gastric Dilatation-Volvulus Syndrome in Dogs: A Practitioner/Owner Case-Control Study. J. Am. Anim. Hosp. Assoc. 33:197–204, 1997.
Patronek, G, Waters, D, Glickman, L. Comparative Longevity of Pet Dogs and Humans: Implications for Gerontology Research. J. Gerontol. 52A:B171–178, 1997.
Dodds, W. J. Autoimmune Thyroiditis and Polyglandular Autoimmunity of Purebred Dogs. Can. Pract. 22 (1): 18–19, 1997.
Hancock, W. W. Chemokines and the Pathogenesis of T Cell-Dependent Imune Responses. Am. J. Pathol. 148: 681–684, 1996.
Dodds, W. J. Estimating Disease Prevalence with Health Surveys and Genetic Screening. Adv. Vet. Sci. Comp. Med. 39: 29–96, 1995.
Happ, G. M. Thyroiditis—A Model Canine Autoimmune Disease. Adv. Vet. Sci. Comp. Med. 39: 97–139, 1995.
Merrill, J. E., Jonakait, A. G. M. Interactions of the Nervous Systems in Development, Normal Brain Homeostasis, and Ddisease. FASEB J. 9: 611–618, 1195.
Cavallo, M. G., Pozzilli, P., Thorpe, R. Cytokines and Autoimmunity. Clin. Exp. Immunol. 1: 1–7, 1994.
Patronek, G. J., Glickman, L. T. The Epidemiological Approach to Risk Management: Factors which Increase Chance of Disease. Vet. Forum 11(8); 66–67, 1994.
Jackwood, M. W. Biotechnology and the Development of Diagnostic Tests in Veterinary Medicine. J. Am. Vet. Med. Assoc. 204: 1603–1605, 1994.
Dodds, W. J., Raymond, S. L., Brooks, M. B. Inherited and Acquired von Willebrand's Disease. Parts 1–2. Vet. Pract. STAFF 5(4–5): 1, 14–17; 21–23, 1993.
Stefanon, G., Stefanon, B., Stefanon, G. G., Dodds, W. J. Inherited and Acquired Bleeding Disorders in Northeastern Italy. Can. Pract. 18(3); 15–23, 1993.
Dodds, W. J. Genetically Based Immune Disorders: Autoimmune and Other Diseases. Parts 1–3. Vet. Pract. STAFF 4(1–3): 8–10, 1, 26–31; 35–37, 1992.
Dodds, W. J. Genetically Based Imune Disorders: Immune Deficiency Diseases. Vet. Pract. STAFF 4(5); 19–21, 1992.
Brooks, M. B., Dodds, W. J., and Raymond, S. L. Epidemiologic Features of von Willebrand's Disease in Doberman Pinschers, Scottish Terrers and Shetland Sheepdogs. 260 cases (1984–1988). J. Am. Vet. Med. Assoc. 200:1123–1127, 1992.
Dodds, W. J. Autoimmune Thyroid Disease. Dog World 77(4): 36–40, 1992.
Dodds, W. J. Unraveling the Autoimmune Mystery. Dog World 77(5): 44–48, 1992.
Dodds, W. J. Thyroid Can Alter Behavior. Dog World 77(10):40–42, 1992.
Goetzl, E.J., Sreedharan, S.P. Mediators of communication and adaptation in the neuroendocrine and immune systems. FASEB J. 6: 2646–2652, 1992.
Elmslie, R. E., Dow, S. W., Ogilvie, G. K. Interleukins: Bilolgical Properties and Therapeutic Potential. J. Vet. Int. Med. 5: 283–293, 1991.
Raymond, S. L., Jones, D. W., Brooks, M. B., Dodds, W. J. Clinical and Laboratory Features of a Severe Form of von Willebrand's Disease in Shetland Sheepdogs. J. Am. Vet. Med. Assoc. 197:1342–1346, 1990.

Patterson, D. F., Haskins, M. E., Jezyk, P. F., Giger, U. et al. Research on Genetic Diseases:Reciprocal Benefits to Animals and Man. J. Am. Vet. Med. Assoc. 193: 1131–1144, 1988.

Jolly, R. D., Dodds, W. J., Ruth, G. R., Trauner, D. B. Screening for Genetic Diseases: Principles and Practice. Adv. Vet. Sci. Comp. Med. 25: 245–276, 1981.

What is claimed is:

1. A veterinary diagnostic method of health profiling a selected subject animal to enhance the quality of life or extend the lifespan of the selected animal, the animal being non-livestock, comprising:
 a) obtaining the
  i) genetic data of the selected animal, the genetic data including at least one of the data relating to genetic mapping, genetic background, or genetic screening related to the selected animal; and
  ii) phenotype health assessment data of the selected animal;
 b) using a computer program, combining the genetic data and the phenotype health assessment data to determine a relationship between the genetic data and the phenotype health assessment data;
 c) selecting from b) at least one of:
  i) the data relating to the temperament of the selected animal;
  ii) the data relating to the lifespan of the selected animal; or
  iii) a physiologic or genetic marker for autoimmune thyroiditis or thyroid dysfunction of the selected animal; and
 d) analyzing the selection of the data of c), the analysis including an evaluation of health, disease or disorder probabilities to thereby enhance the quality of life or extend the lifespan of the selected animal, the selected animal being at least one of a selected animal family, selected animal breed, selected animal grouping, or selected animal species.

2. The method of claim 1, including the steps of communicating between a remote user and a central database processing resource through a computer network, and providing a report of the analysis to the remote user after charging for such report.

3. A method of claim 2, wherein the computer network is the Internet.

4. A method of claim 1 comprising the step of analyzing biological laboratory test data from a bodily fluid or a tissue of the selected animal, such test data being related to a neurotransmitter activity of the animal.

5. The method of claim 4, including obtaining data related to at least one of the value of serotonin, the gamma-aminobutyric acid (GAB), the glutamate, the dopamine, the glycine, the aspartate, the acetylcholine, the norepinephrine, the histamine, the substance P, the vasopressin, the vasoactive intestinal peptide, the neurotensin, or the other neuropeptides of the animal.

6. The method of claim 4, comprising the step of storing the report in a central database processing resource, including permitting a remote user to access the central database processing resource via a communications link, the communications link being a computer network, the access being for obtaining a report from the central database processing resource, the report including the health profile of that animal.

7. The method of claim 1 including obtaining additionally at least one of:
 iv) the neurotransmitter data relating to the temperament of the animal;
 v) the neurotransmitter data relating to the longevity of the animal;
 vi) data assessing the bodily fluid and tissue immune stimulation reaction, neoplastic or paraneoplastic change, or cellular inflammatory response of the animal;
 vii) metabolic marker of the animal for inherited organ dysfunction or dysplasia;
 viii) data assessing the presence of or susceptibility to mammary cancer of the animal;
 ix) data assessing the integrity of immune surveillance mechanisms of the animal; or
 x) data assessing the risk of inherited bleeding disease or disorder of the animal.

8. A method as claimed in claim 1 wherein the genetic data is cross-related to the phenotypic data.

9. A veterinary diagnostic method of health profiling a selected subject animal to enhance the quality of life or extend the lifespan of the selected animal, the animal being non-livestock, comprising:
 a) obtaining the
  i) genetic data of the selected animal, the genetic data including at least one of the data relating to genetic mapping, genetic background, or genetic screening related to the selected animal; and
  ii) phenotype health assessment data of the selected animal;
 b) using a computer program, combining the genetic data and the phenotype health assessment data to determine a relationship between the genetic data and the phenotype health assessment data;
 c) selecting from b) at least one of:
  i) the data relating to the temperament of the selected animal;
  ii) the data relating to the lifespan of the selected animal; or
  iii) a physiologic or genetic marker for autoimmune thyroiditis or thyroid dysfunction of the selected animal; and
 d) analyzing the selection of the data of c), the analysis including an evaluation of health, disease or disorder probabilities and the nutrition of the selected animal, the selected animal being at least one of a selected animal family, selected animal breed, selected animal grouping, or selected animal species.

10. A method as claimed in claim 1 including using the combination of data to create a computer driven statistical model for predicting the occurrence of disease, quality of life or a lifespan of an animal.

11. A method as claimed in claim 9 including using the combination of data to create a computer driven statistical model for predicting the occurrence of disease, quality of life or a lifespan of an animal and the nutrition of the animal.

12. The method of claim 9, including permitting communication of an access request message from a remote user via a communications link, and the communications link being a computer network, the access request being for obtaining a report of the analysis.

13. A method of claim 12, wherein the computer network is the Internet.

14. A method of claim 9 wherein the genetic data is cross-related to the phenotypic data.

* * * * *